US009259392B2

(12) United States Patent
Gould-Fogerite et al.

(10) Patent No.: US 9,259,392 B2
(45) Date of Patent: *Feb. 16, 2016

(54) COCHLEATE COMPOSITIONS DIRECTED AGAINST EXPRESSION OF PROTEINS

(71) Applicant: Rutgers, The State University of New Jersey, New Brunswick, NJ (US)

(72) Inventors: Susan Gould-Fogerite, Annandale, NJ (US); Raphael J. Mannino, Glen Gardner, NJ (US); Patrick Ahl, Princeton, NJ (US); Gaofeng Shang, Livingston, NJ (US); Zi Wei Chen, Newark, NJ (US); Sara L. Krause-Elsmore, Kearny, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/038,810

(22) Filed: Sep. 27, 2013

(65) Prior Publication Data

US 2014/0186430 A1    Jul. 3, 2014

Related U.S. Application Data

(63) Continuation of application No. 13/298,902, filed on Nov. 17, 2011, now Pat. No. 8,546,555, which is a continuation of application No. 12/658,636, filed on Feb. 11, 2010, now abandoned, which is a continuation of application No. 11/653,093, filed on Jan. 11, 2007, now abandoned, which is a continuation of application No. 10/822,235, filed on Apr. 9, 2004, now abandoned.

(60) Provisional application No. 60/463,076, filed on Apr. 15, 2003, provisional application No. 60/499,247, filed on Aug. 28, 2003, provisional application No. 60/502,557, filed on Sep. 11, 2003, provisional application No. 60/532,755, filed on Dec. 24, 2003.

(51) Int. Cl.
C12N 15/11    (2006.01)
A61K 9/127    (2006.01)
A61K 31/7048  (2006.01)
C12N 15/113   (2010.01)
A61K 38/00    (2006.01)

(52) U.S. Cl.
CPC .............. *A61K 9/127* (2013.01); *A61K 9/1274* (2013.01); *A61K 31/7048* (2013.01); *C12N 15/111* (2013.01); *C12N 15/113* (2013.01); *C12N 15/1135* (2013.01); *C12N 15/1137* (2013.01); *C12Y 102/01012* (2013.01); *A61K 38/00* (2013.01); *C12N 2310/14* (2013.01); *C12N 2310/3233* (2013.01); *C12N 2310/53* (2013.01); *C12N 2320/32* (2013.01)

(58) Field of Classification Search
CPC ............................. A61K 9/127; C12N 15/113
See application file for complete search history.

(56) References Cited

U.S. PATENT DOCUMENTS

| | | | |
|---|---|---|---|
| 4,078,052 | A | 3/1978 | Papahadjopoulos |
| 4,725,442 | A | 2/1988 | Haynes |
| 4,871,488 | A | 10/1989 | Mannino et al. |
| 4,874,795 | A | 10/1989 | Yesair |
| 4,906,476 | A | 3/1990 | Radhakrishnan |
| 4,944,948 | A | 7/1990 | Uster et al. |
| 4,990,291 | A | 2/1991 | Schoen et al. |
| 5,026,557 | A | 6/1991 | Estis et al. |
| 5,100,591 | A | 3/1992 | Leclef et al. |
| 5,269,979 | A | 12/1993 | Fountain |
| 5,409,698 | A | 4/1995 | Anderson et al. |
| 5,571,517 | A | 11/1996 | Yesair |
| 5,580,859 | A | 12/1996 | Felgner et al. |
| 5,589,466 | A | 12/1996 | Felgner et al. |
| 5,643,574 | A | 7/1997 | Gould-Fogerite et al. |
| 5,834,015 | A | 11/1998 | Oleske et al. |
| 5,840,707 | A | 11/1998 | Mannino et al. |
| 5,994,318 | A | 11/1999 | Gould-Fogerite et al. |
| 6,120,751 | A | 9/2000 | Unger |
| 6,153,217 | A | 11/2000 | Jin et al. |
| 6,340,591 | B1 | 1/2002 | Margolis et al. |
| 6,403,056 | B1 | 6/2002 | Unger |
| 6,406,713 | B1 | 6/2002 | Janoff et al. |
| 6,447,800 | B2 | 9/2002 | Hope |
| 6,592,894 | B1 | 7/2003 | Zarif et al. |
| 6,808,720 | B2 | 10/2004 | Unger |
| 8,546,555 | B2 | 10/2013 | Gould-Fogerite et al. |
| 2003/0143740 | A1 | 7/2003 | Wooddell et al. |

(Continued)

FOREIGN PATENT DOCUMENTS

| | | |
|---|---|---|
| FR | 2 221 122 A | 10/1974 |
| WO | WO 96/025942 | 8/1996 |
| WO | WO 97/030725 | 8/1997 |
| WO | WO 00/042989 | 7/2000 |
| WO | WO 01/052817 | 7/2001 |
| WO | WO 02/44321 | 6/2002 |
| WO | WO 02/097114 | 12/2002 |
| WO | WO 2004/012709 | 2/2004 |

OTHER PUBLICATIONS

Florea et al. AAPS PharmSci 2002: 4, pp. 1-11.*
Dudley et al. Current Opinion in Molecular Therapeutics 2003, 5:113-117.*
Anderson et al. "Formulation and evaluation of a folic acid receptor-targeted oral vancomycin liposomal dosage form." Pharm Res. 2001; 18(3):316-22.

(Continued)

*Primary Examiner* — Brian Whiteman
(74) *Attorney, Agent, or Firm* — MH2 Technology Law Group, LLP

(57) ABSTRACT

Disclosed herein are novel siRNA-cochleate and morpholino-cochleate compositions. Also disclosed are methods of making and using siRNA-cochleate and morpholino-cochleate compositions.

16 Claims, 7 Drawing Sheets
(4 of 7 Drawing Sheet(s) Filed in Color)

(56) References Cited

U.S. PATENT DOCUMENTS

| | | |
|---|---|---|
| 2003/0175950 A1 | 9/2003 | McSwiggen |
| 2003/0235577 A1 | 12/2003 | Shapiro et al. |
| 2004/0092727 A1 | 5/2004 | Jin |
| 2005/0013855 A1 | 1/2005 | Gould-Fogerite et al. |
| 2005/0186265 A1* | 8/2005 | Zarif et al. ............ A61K 9/1274 424/450 |
| 2008/0009457 A1 | 1/2008 | Gould-Fogerite et al. |
| 2011/0091523 A1 | 4/2011 | Gould-Fogerite et al. |

OTHER PUBLICATIONS

Brummelkamp, et al., "A system for stable expression of short interfering RNAs in mammalian cells." Science Apr. 19, 2002; 296(5567):550-3.

Burghoom, et al. "Molecular evaluation of the plasma membrane proton pump from *Aspergillus fumigatus*." Antimicrob Agents Chemother. Mar. 2002; 46(3):615-24.

Couvreur et al. "Nano- and microparticles for the delivery of polypeptides and proteins." Adv. Drug Delivery Rev. 1993; 10:141-162.

Gould-Fogerite, et al. Chimerasome-mediated gene transfer in vitro and in vivo. Gene. Dec. 14, 1989;84(2):429-38.

Gould-Fogerite, et al. Rotary dialysis: its application to the preparation of large liposomes and large proteoliposomes (protein-lipid vesicles) with high encapsulation efficiency and efficient reconstitution of membrane proteins. Anal Biochem. Jul. 1985;148(1):15-25.

Gould-Fogerite, et al. The reconstitution of biologically active glycoproteins into large liposomes: use as a delivery vehicle to animal cells. Advances in Membrane Biochemistry and Bioenergetics. 1988 pp. 569-586.

Gould-Fogerite, et al. Liposome preparation and related techniques. Liposome Technology, $2^{nd}$ Edition. 1993 1:67-80.

Gould-Fogerite, et al. Interaction of liposomes with the biological milieu. Liposome Technology, $2^{nd}$ Edition. 1993. 3:261-276.

Gould-Fogerite, et al.l *Mucosal and systemic immunization using cochleate and liposome vaccines."J. Liposome Res.* 1996; 6(2):357-79.

Gould-Fogerite, et al. "Targeting immune response inducting with cochleate and lipsome based vaccines." *Adv. Drug Delivery Rev.* 1998; 32(3):273-87.

Gould-Fogerite, et al. "Cochleates for induction of mucosal and systemic immune responses." *Meth Molec Med*. 1999; 42:179-86.

Gould-Fogerite, et al. "Cochleates delivery vehicles: Applications in vaccine Delivery." *J. Liposome Res*. 2000; 10(4):339-58.

Gould-Fogerite, et al. "Cochleates delivery vehicles: Applications to gene therapy." Mar./Apr. 2003; 3(2)41-7.

Hu et al., "ERB-B-2/NEU DNA vaccine based immunotherapy." International Congress of Immunology Abstracts. Budapest, Hungary Jul. 23, 1995; 870.

Lavelle, et al. Improved methods for the delivery of liposome-sequestered RNA into eucaryotic cells. Arch Biochem Biophys. May 1982;215(2):486-97.

Lichtenber. Et al., "Liposomes: Preparation, characterization, and preservation." Meth Biochem Anal. 1988; 33:337-462.

Longenecker et al. "Three dimensional structure of mammalian case in kinase I: Molecular basis for phosphate recognition." J. Mol. Biol. 1996; 257:618-31.

Lu et al., "siRNA-mediated antitumorigenesis for drug target validation and therapeutics." Curr. Opin. Mol. Ther. Jun. 2003; 5(3):225-34.

Mannino, et al. Liposome mediated gene transfer. Biotechniques. Jul.-Aug. 1988;6(7):682-90.

Mannino, et al. Liposomes as adjuvants for peptides: preparation and use of immunogenic peptide-phospholipid complexes. Liposome Technology $2^{nd}$ Ed. 1993; 2:167-84.

Mannino, et al. Lipid matrix-based vaccines for mucosal and systemic immunization. Pharm Biotechnol. 1995;6:363-87.

Mannino, et al. Antigen cochleate preparation for oral and systemic vaccinations. New Gen. Vaccines. $2^{nd}$ ed. 1997; Ch 18, 229-39.

Papahadjopolous, et al. "Cochleate lipid cylinders formation by fusion of unilamellar vesicles," *Biochimica et Biophysica Acta*, vol. 394, No. 3, pp. 483-491, 1975.

Papahadjopoulos, et al. The use of lipid vesicles for introducing macromolecules into cells. Protein Turnover Lysosome Funct. 1978 543-60.

Parker et al., "In vivo and in vitro antiproliferative effects of antisense interleukin 10 oligonucleotides." Meth Enzym; Antisense Tech, Part B. 1999; 314:411-29.

Paroo et al. "Challenges for RNAi in vivo." Trends Biotechnol. Aug. 2004; 22(8):390-4.

Sanderson et al., "Encapsulation of cancomycin and gentamycin with cationic liposomes for inhibition of growth of *Straphylococcus epidermidis*." J. Drug Target. 1996; 4(30:181-9.

Santangelo et al., "Efficacy of oral cochleate-amphotericin B in a mouse model of systemic candidiasis." Antimicrob, Agents Chemother. 2000; 2356-60.

Sundram et al., "General and efficient method for the solution and solid-phase synthesis of vancomycin carboxaminde derivatives." J. Org. Chem. 1995; 60:1102-3.

Wassef, et al. Liposomes as carriers for vaccines. Immunomethods. Jun. 1994;4(3):217-22.

Yamamoto et al., "Human C-ERB-B-2 MRNA." Genbank Mar. 30, 1995; XP002264793.

Zarif, L., et al., "Amphotericin B cochleates as a novel oral delivery system for the treatment of fungal infection," Proceedings of the International Symposium on Controlled Release of Bioactive Materials, Illinois: Controlled Release Society, pp. 964-965,1999.

Zarif, L., et al., "Antifungal activiety of amphotericin B cochleates against *Candida albicans* infection in a mouse model." Antimicrob. Agents Chemother. 2000; 1463-9.

Zarif, L., et al., "Cochleates: New Lipid based drug delivery system." J. Liposome Res. 2000; 10(4):523-38.

Zarif, L., et al., "Elongated supramolecular assemblies in drug delivery." J. Controlled Rel. 2002; 81:7-23.

International Search Report and Written Opinion for Application No. PCT/US2004/011020.

Press Clippings-Managing Complexity: Early Days for RNAi (Wess et al.) Mar. 17, 2003, [online], retrieved on May 17, 2006] retrieved from compugen using internet <URL:http:/www.cgen.com/news/articles/article031703.html>.

Heasman, Janet; Morpholino Oligos: Making Sense of Antisense?; Dev. Biol., 243(2): 209-214 (2002).

Wightman, Lionel; Different behavior of branched and linear polyethylenimine for gene delivery in vitro and in vivo; J. Gene Med., 3(4): 362-372 (2001).

* cited by examiner

Red - Rhodamine in Cochleate Lipid  Green - FITC in Morpholino
Yellow, Yellow-Green or Orange - Cochleate And Morpholino Co-localization Time After Cochleate Addition

COCHLEATE COMPOSITIONS DIRECTED AGAINST EXPRESSION OF PROTEINS

RELATED APPLICATIONS

This application is a continuation of U.S. Ser. No. 13/298,902 filed Nov. 17, 2011 and now U.S. Pat. No. 8,546,555 which, in turn, is a continuation of U.S. Ser. No. 12/658,636 filed Feb. 11, 2010 and now abandoned which, in turn, is a continuation of U.S. Ser. No. 11/653,093 filed Jan. 11, 2007 and now abandoned which, in turn, is a continuation of U.S. Ser. No. 10/822,235 filed Apr. 9, 2004 and now abandoned, which claims the benefit of U.S. Provisional Application Ser. No. 60/463,076, filed Apr. 15, 2003; U.S. Provisional Application Ser. No. 60/502,557, filed Sep. 11, 2003; U.S. Provisional Application No. 60/499,247 filed Aug. 28, 2003; and U.S. Provisional Application No. 60/532,755, filed Dec. 24, 2003. The entire contents of each of the aforementioned applications are hereby expressly incorporated herein by reference in their entireties.

BACKGROUND OF THE INVENTION

In diverse eukaryotes, double-stranded RNA (dsRNA) triggers the destruction of mRNA sharing sequence with the double-strand (Hutvdgner et al. (2002) Curr. Opin. Genet. Dev. 12:225-232; Hannon (2002) Nature 418:244-25 1). In animals and basal eukaryotes, this process is called RNA interference (RNAi) (Fire et al. (1998) Nature 391:806-811). There is now wide agreement that RNAi is initiated by the conversion of dsRNA into 21-23 nucleotide fragments by the multi-domain RNase III enzyme, Dicer (Bernstein et al. (2001) Nature 409:363-366; Billy et al. (2001) Proc. Natl. Acad. Sci. USA 98:14428-14433; Grishok et al. (2001) Cell 106:23-34; Ketting et al. (2001) Genes Dev. 15:2654-2659; Knight et al. (2001) Science 293:2269-2271; and Martens et al. (2002) Cell 13:445-453). These short RNAs are known as small interfering RNAs (siRNAs), and they direct the degradation of target RNAs complementary to the siRNA sequence (Zamore et al. (2000) Cell 101:25-33; Elbashir et al. (2001) Nature 411:494498; Elbashir et al. (2001) Genes Dev. 15:188-200; Elbashir et al. (2001) EMBO J 20:6877-6888; Nykdnen et al. (2001) Cell 107:309-321; and Elbashir et al. (2002) Clin. Pharinacol. 26:199-213).

siRNA molecules typically have 2- to 3-nucleotide 3'-overhanging ends, which permits them to be capable of interacting with an endonuclease complex, which results in a targeted mRNA cleavage. The potential therapeutic use of siRNA has been demonstrated in a number of systems. RNAi technology has been utilized to successfully target various genes, including HIV rev genes, CD4 and CD8 genes, and P53 genes (Lee, N. S. et al. (2002) Nature Biotechnol. 20: 500-505; Brummelkamp, T. R., et al. Science 2002. 296: 550-553.).

siRNAs have been used in a number of different experimental settings to silence gene expression. For example, chemically synthesized or in vivo transcribed siRNAs have been transfected into cells, injected into mice, or introduced into plants (e.g. by a particle gun). Additionally, siRNAs have been expressed endogenously from siRNA expression vectors or PCR products in cells or in transgenic animals.

Besides being utilized for gene silencing, siRNAs have been determined to play diverse biological functions in vivo. This includes roles that include antiviral defense, transposon silencing, gene regulation, centromeric silencing, and genomic rearrangements. Such functional diversity has exemplified the importance of siRNAs within cells and has also stirred interest in their detection across species and tissues. Gene Specific Silencing by RNAi, Tech Notes 10(1). McManus M T and Sharp P A (2002) Gene silencing in mammals by small interfering RNAs. Nature Rev Genet 3: 737-747. Dillin A (2003) Proc Natl Acad Sci USA 100(11): 6289-6291. Tuschl T (2002) Nature Biotechnol 20: 446-448.

An obstacle to the realization of the full potential of gene therapy is the development of safe and effective means for delivering siRNA to cells and organisms. The use of antisense oligonucleotides as therapeutic agents has also been widely investigated in the past few years. Gould-Fogerite et al. Cochleate Delivery Vehicles: Applications to Gene Therapy. Drug Delivery Technology, Vol 3:40-47, 2003. Parker et al. In Vivo and in vitro anti-proliferative effects of antisense IL-10 Oligonucleotides in Antisense Technology, Part B, M. Ian Phillips, Ed., Methods in Enzymology, Vol 314, pp 411-429, 1999; Mannino et al., New Generation Vaccines: "Antigen cochleate formulations for oral and systemic vaccination," p. 1-9 (Marcel Dekker, New York, $2^{nd}$ ed. 1997); Brent et al., Neurosci 114(2): 275-278 (2002); Akhtar et al., Nucleic Acids Res. 19:5551 (1991). Their efficacy is based on their ability to recognize their mRNA target in the cytoplasm and to block gene expression by binding and inactivating selected RNA sequences.

While the potential of antisense is widely recognized, there are numerous limitations to the use of antisense currently available. One of the key limiting aspects of this strategy is poor cell penetration. Akhtar et al., Nucleic Acids Res. 19:5551 (1991).

Morpholino oligonucleotides (also referred to herein as "morpholinos") are oligonucleotides that include an antisense oligonucleotide and morpholine backbone. These antisense morpholinos, typically 18-25 nucleotides in length, can be designed to bind to a complementary sequence in a selected mRNA. The binding of the morpholino to the "target sequence" prevents translation of that specific mRNA, thereby preventing the protein product from being made. Morpholinos function by an RNase H-independent mechanism (i.e., a steric block mechanism as opposed to an RNase H-cleavage mechanism), and are soluble in aqueous solutions, with most being freely soluble at mM concentrations (typically 10 mg/ml to over 100 mg/ml). Nasevicius et al., Nat. Genet 26:216-220 (2000); Lewis et al., Development 128:3485-95 (2001); Mang'era et al., Eur. J. Nucl. Med. 28:1682-1689 (2001); Satou et al., Genesis 30:103-06 (2001); Tawk et al., Genesis 32:27-31 (2002); Lebedeva et al., Annu. Rev. Pharmacol. Toxicol. 4:403-19 (2001).

Morpholinos have numerous, significant advantages over the alternative phosphorothioates, which have been documented with a number of non-antisense effects. Morpholinos generally are stable in cells because their morpholine backbone is not recognized by nucleases. In addition, morpholinos are highly effective with predictable targeting, as compared to other antisense molecules. Nasevicius et al., Nat. Genet 26:216-220 (2000); Lewis et al., Development 128:3485-95 (2001); Mang'era et al., Eur. J. Nucl. Med. 28:1682-1689 (2001); Satou et al., Genesis 30:103-06 (2001); Tawk et al., Genesis 32:27-31 (2002); Lebedeva et al., Annu. Rev. Pharmacol. Toxicol. 4:403-19 (2001).

Key parameters for antisense inhibition by antisense oligodeoxiribonucleotides are their intracellular delivery and concentration. At the present time, it is believed that naked oligonucleotides enter the cell via active processes of adsorptive endocytosis and pinocytosis. However, the penetration of the endosomal barrier is a pre-requisite event for antisense activity and the naked antisense oligonucleotides do not appear to do this in great extent. Lebedeva et al., Annu. Rev. Pharmacol. Toxicol. 4:403-19 (2001); Weiss et al., Neurochem. Int. 31:321-48 (1997). Although complexes of antisense oligonucleotides with cationic liposomes, in some instances, have enhanced intracellular delivery, they have come with a disadvantage, cytotoxicity. Their utility in vitro and in vivo has also been limited by their lack of stability in serum and their inflammatory properties.

Conventional methods for the delivery of morpholinos in vitro include scrape loading and the so-called "special delivery vehicles." Scrape loading entails adding oligonucleotides to adherent cells and scraping the cells from their plate, which disrupts the cell membrane temporarily allowing the oligonucleotide to enter the cell cytoplasm. Scraping the cells causes damage to the membrane, thereby reducing the viability of the cell population and ultimately altering the cellular characteristics of the remaining viable cells. Of the cells that do survive, not all may have received the morpholino. The second method, the "special delivery vehicle" supplied with the morpholino, requires dramatic changes in pH that result in very low efficacy. The low efficacy of the "special delivery vehicle" may be due to cytotoxicity or other changes to the cells.

The above methods are not translatable to in vivo delivery because they involve compromise of the target cells and pH changes. Furthermore, any in vivo delivery method or product must deliver the oligonucleotide to the cytosol. Without delivery to the cytosol, oligonucleotides remain trapped in the endosome/lysosome, or may be exocytosed.

SUMMARY OF THE INVENTION

The present invention provides compositions and methods of delivering siRNA and morpholinos to cells and organisms employing cochleates. Also provided are novel methods of forming cochleates and methods of treatment and administration.

In one aspect, the invention provides an siRNA-cochleate composition including a cochleate, and an siRNA associated with the cochleate. In certain embodiments, the siRNA comprises at least one mismatch, at least one substitution, and/or is about 21-23 nucleotides long.

In one embodiment, the siRNA mediates RNA interference against a target mRNA. The target mRNA can be, e.g., an mRNA that expresses a protein selected from the group consisting of: a cancer protein, a virus protein, an HIV protein, a fungus protein, a bacterial protein, an abnormal cellular protein, a normal cellular protein. The composition can also include a second siRNA directed against a second target mRNA. In certain preferred embodiments, the composition includes a plurality of siRNA against the same target mRNA.

In one embodiment, the cochleate includes a negatively charged lipid component and a multivalent cation component. Additionally or alternatively, the siRNA is complexed with a transfection agent prior to contacting the liposomes. The transfection agent can be a polycationic transfection agent, e.g., polyethylenimine (PEI) or a derivative thereof. The compositions of the invention can further include at least one additional cargo moiety and/or at least one aggregation inhibitor.

In another aspect, the invention provides a method of administering an siRNA to a host comprising: administering a biologically effective amount of an siRNA-cochleate composition to a host comprising a cochleate and an siRNA associated with the cochleate. In one embodiment, the siRNA is delivered from the cochleate to a cell in the host. In another, the siRNA is delivered into a cytosol compartment of the cell.

In preferred embodiments, the siRNA mediates RNA interference against a target mRNA in the host. In one embodiment, the target mRNA expression in the host is reduced by at least about 50%. In other embodiments, the target protein synthesis in the host is reduced by at least about 10%, or at least about 50%. In certain embodiments, the host is a cell, a cell culture, an organ, tissue, or an animal. The method may also include the step of examining the function of the target mRNA or protein expressed by the target mRNA in the host.

In yet another aspect, the invention provides a method of treating a subject having a disease or disorder associated with expression of a target mRNA. The method includes administering to a subject a therapeutically effective amount of an siRNA-cochleate composition, including a cochleate and an siRNA against a target mRNA associated with a disease or disorder, such that the disease or disorder is treated.

In some embodiments, the disease or disorder is selected from the group consisting of: a neurological disorder associated with aberrant or unwanted gene expression, schizophrenia, obsessive compulsive disorder (OCD), depression, a bipolar disorder, Alzheimer's disease, Parkinson's disease, a lysosomal storage disease, Fabry's disease, Gaucher's Disease, Type I Gaucher's Disease, Farber's disease, Niemann-Pick disease (types A and B), globoid cell leukodystrophy (Krabbe's disease), metachromic leukodystrophy, multiple sulfatase deficiency, sulfatidase activator (sap-B) deficiency, sap-C deficiency, $G_{M1}$-gangliosidosis, Tay-Sachs disease, Tay-Sachs B1 variant, Tay-Sachs AB variant, Acid Maltase Deficiency, Mucopolysaccharidosis, Sandhoff's disease, a cancer, a cell proliferative disorder, a blood coagulation disorder, Dysfibrinogenaemia, hemophilia (A and B), dematological disorders, hyperlipidemia, hyperglycemia, hypercholesterolemia, obesity, acute and chronic leukemias and lymphomas, sarcomas, adenomas, a fungal infection, a bacterial infection, a viral infection, an autoimmune disorder, systemic lupus erythematosis, multiple sclerosis, myasthenia gravis, autoimmune hemolytic anemia, autoimmune thrombocytopenia, Grave's disease, allogenic transplant rejection, rheumatoid arthritis, ankylosing spondylitis, psoriasis, scleroderma, carcinomas, epithelial cancers, small cell lung cancer, non-small cell lung cancer, prostate cancer, breast cancer, pancreatic cancer, hepatocellular carcinoma, renal cell carcinoma, biliary cancer, colorectal cancer, ovarian cancer, uterine cancer, melanoma, cervical cancer, testicular cancer, esophageal cancer, gastric cancer, mesothelioma, glioma, glioblastoma, pituitary adenomas, inflammatory diseases, osteoarthritis, atherosclerosis, inflammatory bowel diseases (Crohns and ulcerative colitis), uveitis, eczema, chronic rhinosinusitis, asthma, a hereditary disease, cystic fibrosis, and muscular dystrophy.

In yet another aspect, the invention provides a method of forming an siRNA-cochleate composition that includes precipitating a liposome and an siRNA to form an siRNA-cochleate. In one embodiment, the method includes adjusting the pH of the siRNA and/or charging the base pairs of the siRNA.

In some embodiments, the siRNA is complexed with a transfection agent prior to precipitating. The transfection agent can be mixed with the liposomes prior to adding the siRNA. In one embodiment, the transfection agent is PEI or a derivative thereof or other polyvalent cation.

The method can include using an elevated amount of calcium for precipitating the liposome and the siRNA. Additionally or alternatively, the method can include the step of extruding the liposome with the siRNA prior to precipitation. In certain embodiments, the siRNA-liposome can be prepared by adding a chelating agent to a cochleate to form a liposome in the presence of siRNA.

In yet another aspect, the invention provides a morpholino-cochleate composition that includes a cochleate; and a morpholino oligonucleotide associated with the cochleate.

In one embodiment, the morpholino oligonucleotide is an antisense morpholino oligonucleotide. The morpholino oligonucleotide can include at least one mismatch and/or can be about 18-25 nucleotides long. In preferred embodiments, the morpholino oligonucleotide mediates inhibition of translation of a target mRNA. In preferred embodiments, the morpholino oligonucleotide is also directed against the synthesis of a protein.

In certain embodiments, the cochleate comprises a negatively charged lipid component and a cation component, includes at least one additional cargo moiety and/or includes at least one aggregation inhibitor. The composition can also include a second morpholino oligonucleotide directed against the synthesis of the protein or a second protein. In other embodiments, the composition includes a plurality of morpholinos directed against the same target mRNA.

In yet another aspect, the invention provides a method of administering a morpholino oligonucleotide to a host. The method generally includes administering a biologically effective amount of a morpholino-cochleate composition to the host comprising a cochleate and a morpholino oligonucleotide associated with the cochleate.

In one embodiment, the morpholino oligonucleotide is released from the cochleate into a cell in the host. In preferred embodiments, the morpholino oligonucleotide mediates inhibition of translation of a target mRNA.

In certain embodiments, target mRNA expression in the host is reduced by at least about 50%, target protein synthesis in the host is reduced by at least about 10%, and/or target protein synthesis in the host is reduced by at least about 50%.

In certain embodiments, the host is a cell, a cell culture, an organ, tissue, or an animal, and/or the morpholino oligonucleotide is delivered into a cytosol compartment of a cell.

In yet another aspect, the invention provides a method of forming a morpholino-cochleate composition that includes the step of precipitating a liposome and a morpholino to form a morpholino-cochleate.

The method can include the step of adjusting the pH of the morpholino and/or charging the base pairs of the morpholino. The method can include adjusting the pH of the morpholino to induce a charge in the morpholino. In one embodiment, the pH of the morpholino is between about 8.0 and about 9.0.

The method can include using an elevated amount of calcium for precipitating the liposome and the morpholino. The method can include extruding the liposome prior to precipitation. In one embodiment, the liposome is prepared from addition of a chelating agent to a cochleate to form a liposome in the presence of morpholino. In some embodiments, the method includes adding at least one additional cargo moiety to the morpholino and the liposome prior to or after precipitating and/or adding an aggregation inhibitor to the morpholino and the liposome prior to or after precipitating.

In yet another aspect, the invention provides a method of treating a subject having a disease or disorder associated with expression of a target mRNA. The method generally includes administering to a subject a therapeutically effective amount of an morpholino-cochleate composition, comprising a cochleate and an siRNA against a target mRNA associated with a disease or disorder, such that the disease or disorder is treated. The disease or disorder can be selected from the group consisting of: a neurological disorder associated with aberrant or unwanted gene expression, schizophrenia, obsessive compulsive disorder (OCD), depression, a bipolar disorder, Alzheimer's disease, Parkinson's disease, a lysosomal storage disease, Fabry's disease, Gaucher's Disease, Type I Gaucher's Disease, Farber's disease, Niemann-Pick disease (types A and B), globoid cell leukodystrophy (Krabbe's disease), metachromic leukodystrophy, multiple sulfatase deficiency, sulfatidase activator (sap-B) deficiency, sap-C deficiency, $G_{M1}$-gangliosidosis, Tay-Sachs disease, Tay-Sachs B1 variant, Tay-Sachs AB variant, Acid Maltase Deficiency, Mucopolysaccharidosis, Sandhoff's disease, a cancer, a cell proliferative disorder, a blood coagulation disorder, Dysfibrinogenaemia, hemophelia (A and B), dematological disorders, hyperlipidemia, hyperglycemia, hypercholesterolemia, obesity, acute and chronic leukemias and lymphomas, sarcomas, adenomas, a fungal infection, a bacterial infection, a viral infection, an autoimmune disorder, systemic lupus erythematosis, multiple sclerosis, myasthenia gravis, autoimmune hemolytic anemia, autoimmune thrombocytopenia, Grave's disease, allogenic transplant rejection, rheumatoid arthritis, ankylosing spondylitis, psoriasis, scleroderma, carcinomas, epithelial cancers, small cell lung cancer, non-small cell lung cancer, prostate cancer, breast cancer, pancreatic cancer, hepatocellular carcinoma, renal cell carcinoma, biliary cancer, colorectal cancer, ovarian cancer, uterine cancer, melanoma, cervical cancer, testicular cancer, esophageal cancer, gastric cancer, mesothelioma, glioma, glioblastoma, pituitary adenomas, inflammatory diseases, osteoarthritis, atherosclerosis, inflammatory bowel diseases (Crohns and ulcerative colitis), uveitis, eczema, chronic rhinosinusitis, asthma, a hereditary disease, cystic fibrosis, and muscular dystrophy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B are photographs of rhodamine labeled cochleates incubated with NGF differentiated PC12 cells at 3 hours and 12 hours, respectively, after cochleate introduction. As illuminated by the fluoresced rhodamine, the cochleates fuse with the outer membrane and form submembrane aggregates. FIGS. 1C (low power) and 1D (high power) are photographs of fluoresced rhodamine labeled cochleates containing fluorescein isothiocyanate (FITC) labeled morpholinos. FIGS. 1C-D illustrate cochleates containing morpholinos, morpholinos that have been released into the cytosol from unwrapped cochleates and the delivery of FITC labeled anti-GAPDH Morpholino into the cytoplasm. Scale bars indicate 10 micrometers.

DETAILED DESCRIPTION OF THE INVENTION

Figures 1A, 1B, 1C, 1D:
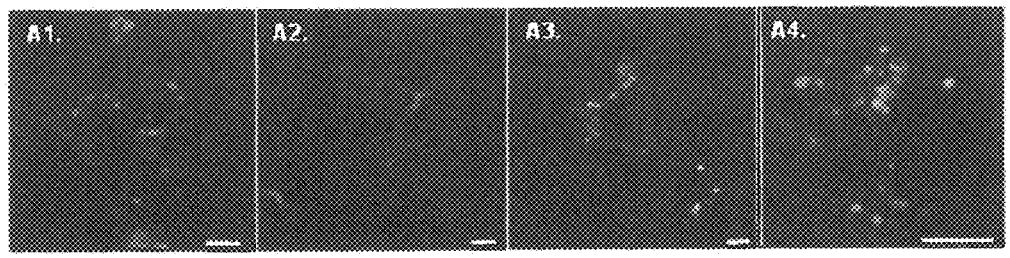
FIGS. 1A-D is photographs of cells treated with morpholino-cochleates.

A novel approach to the delivery of siRNA and morpholino antisense molecules has now been discovered, thus providing improved modes of gene therapy. The present invention employs cochleate delivery vehicles to protect and deliver siRNA and morpholinos against target mRNA in cells, tissues, organs, and to organisms, e.g., animals and humans in a variety of dosage forms (e.g., oral capsules and liquids) in a safe and effective manner

DEFINITIONS

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; and N-modified (e.g., alkylated, e.g., N6methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2'OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11 (5): 317-25, Vorobjev et al. Antisense Nucleic Acid Drug Dev. 2001 Apr. 11.2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vivo.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively).

RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to a double stranded RNA (or RNA analog) comprising between about 10-50 nucleotides (or nucleotide analogs) which is capable of directing or mediating RNA interference.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, an "identical" oligonucleotide has the same sequence as the reference nucleotide subsequence to which the oligonucleotide is being compared. An "exactly complementary" oligonucleotide refers to an oligonucleotide whose complement has the same sequence as the reference nucleotide subsequence to which the oligonucleotide is being compared. A "substantially complementary" and a "substantially identical" oligonucleotide have the ability to specifically hybridize to a reference gene, DNA, cDNA, or mRNA, and its exact complement.

As used herein, the term "RNA interference" ("RNAi") refers to a selective intracellular degradation of RNA to mediate, reduce or silence the expression of a target gene.

An siRNA "that mediates RNAi against a target mRNA" refers to an siRNA including a sequence sufficiently complementary to a target RNA (e.g. mRNA or RNA that can be spliced to produce one or more mRNAs) to trigger the destruction of the target mRNA by the RNAi machinery or process.

A morpholino "that mediates translation of a target mRNA" refers to a morpholino including a sequence sufficiently complementary to a target RNA (e.g. mRNA or RNA that can be spliced to produce one or more mRNAs) to interfere with translation of the mRNA into a protein.

As used herein, the term "isolated RNA" or "isolated siRNA" refers to RNA or siRNA molecules, respectively, which are substantially free of other cellular material, or culture medium when produced by recombinant techniques, or substantially free of chemical precursors or other chemicals when chemically synthesized.

As used herein, the terms "cochleate," "lipid precipitate" and "precipitate" are used interchangeably to refer to a lipid precipitate component that generally includes alternating cationic and lipid bilayer sheets with little or no internal aqueous space, typically stacked and/or rolled up, wherein the cationic sheet is comprised of one or more multivalent cations. Additionally, the term "encochleated" means associated with the cochleate structure, e.g. by incorporation into the cationic sheet, and/or inclusion in the lipid bilayer.

As used herein, the term "multivalent cation" refers to a divalent cation or higher valency cation, or any compound that has at least two positive charges, including mineral cations such as calcium, barium, zinc, iron and magnesium and other elements, such as drugs and other compounds, capable of forming ions or other structures having multiple positive charges capable of chelating and bridging negatively charged lipids. Additionally or alternatively, the multivalent cation can include other multivalent cationic compounds, e.g., cationic or protonized cargo moieties.

The lipid employed in the present invention preferably includes one or more negatively charged lipids. As used herein, the term "negatively charged lipid" includes lipids having a head group bearing a formal negative charge in aqueous solution at an acidic, basic or physiological pH, and also includes lipids having a zwitterionic head group.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A gene or mRNA "involved" in or "associated with" a disorder includes a gene or mRNA, the normal or aberrant expression or function of which effects or causes a disease or disorder or at least one symptom of said disease or disorder.

The phrase "examining the function of a target mRNA" refers to examining or studying the expression, activity, function or phenotype arising therefrom, in the host cell, tissue or organism.

Various methodologies of the instant invention include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an siRNA of the invention into a cell or organism. In another embodiment, a "suitable control" or "appropriate control" is a value, level, feature, characteristic, property, etc. determined in a cell or organism, e.g. a control or normal cell or organism, exhibiting, for example, normal traits. In yet another embodiment, a "suitable control" or "appropriate control" is a predefined value, level, feature, characteristic, property, etc.

The cochleates of the present invention can also include one or more aggregation inhibitors. The term "aggregation inhibitor," as used herein, refers to an agent that inhibits aggregation of cochleates. The aggregation inhibitor typically is present at least on the surface of the cochleate, and may only be present on the surface of the cochleate (e.g., when the aggregation inhibitor is introduced after cochleate formation). Aggregation inhibitors can be added before, after, and/or during cochleate formation.

The terms "coat," "coated," "coating," and the like, unless otherwise indicated, refer to an agent (e.g. an aggregation inhibitor) present at least on the outer surfaces of a cochleate. Such agents may be associated with the bilayer by incorporation of at least part of the agent into the bilayer, and/or may be otherwise associated, e.g., by ionic attraction to the cation or hydrophobic or ionic attraction to the lipid.

"Treatment", or "treating" as used herein, refers to the application or administration of a therapeutic agent (e.g., an siRNA cochleate) to a patient, or application or administration of a therapeutic agent to an isolated tissue or cell line from a patient, who has a disease or disorder, a symptom of disease or disorder or a predisposition toward a disease or disorder, that effects or otherwise contributes to curing, healing, alleviating, relieving, altering, remedying, ameliorating, improving or affecting the disease or disorder, the symptoms of the disease or disorder, or the predisposition toward disease.

The term "biologically effective amount" is that amount necessary or sufficient to produce a desired biological response.

An "antisense" oligonucleotide is an oligonucleotide that is substantially complementary to a target nucleotide sequence and has the ability to specifically hybridize to the target nucleotide sequence.

"Morpholino oligonucleotides" and "morpholinos" are used interchangeably, and refer to oligonucleotides having a morpholino backbone.

Various aspects of the invention are described in further detail in the following subsections.

siRNA-Cochleate Compositions

In one aspect, the present invention features encochleated siRNA compositions. The siRNA-cochleate compositions generally include a cochleate, and an siRNA associated with the cochleate.

Preferably, the siRNA molecule has a length from about 10-50 or more nucleotides. More preferably, the siRNA molecule has a length from about 15-45 nucleotides. Even more preferably, the siRNA molecule has a length from about 19-40 nucleotides. Even more preferably, the siRNA molecule has a length of from about 21-23 nucleotides.

The siRNA of the invention preferably mediates RNAi against a target mRNA. The siRNA molecule can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand.

The target mRNA cleavage reaction guided by siRNAs is sequence specific. In general, siRNA containing a nucleotide sequence identical to a portion of the target gene are preferred for inhibition. However, 100% sequence identity between the siRNA and the target gene is not required to practice the present invention. Sequence variations can be tolerated including those that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of an siRNA contribute equally to target recognition. Mismatches in the center of the siRNA are most critical and essentially abolish target RNA cleavage. In contrast, the 3' nucleotides of the siRNA do not contribute significantly to specificity of the target recognition. Generally, residues at the 3' end of the siRNA sequence which is complementary to the target RNA (e.g., the guide sequence) are not critical for target RNA cleavage.

Sequence identity may readily be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad Sci. USA 87:2264-68, modified as in Karlin and Altschul (1993) Proc. Natl. Acad. Sci. USA 90:5873. Such an algorithm is incorporated into the BLAST programs (version 2.0) of Altschul, et al. (1990) J Mol Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target mRNA is preferred. Alternatively, the siRNA may be defined functionally as a nucleotide sequence (or oligonucleotide sequence) that is capable of hybridizing with a portion of the target mRNA transcript (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 ($\log_{10}$ [Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold 15 Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about or about equal to 10, 12, 15, 17, 20, 22, 25, 27, 30, 32, 35, 37, 40, 42, 45, 47 or 50 bases.

In one embodiment, the siRNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

In another embodiment of the present invention the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar modified ribonucleotides, the 2'OH-group is replaced by a group selected from H, OR, R, halo, SH, SR, $NH_2$, NHR, $NR_2$ or $NO_2$, wherein R is C1-C6 alkyl, alkenyl or alkynyl and halo is F, Cl, Br or I.

Nucleotide analogues also include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

RNA may be produced enzymatically or by partial/total organic synthesis, any modified ribonucleotide can be introduced by in vitro enzymatic or organic synthesis. In one embodiment, an siRNA is prepared chemically. Methods of synthesizing RNA molecules are known in the art, in particular, the chemical synthesis methods as described in Verina and Eckstein (1998), Annul Rev. Biochem. 67:99. In another embodiment, an siRNA is prepared enzymatically. For example, an siRNA can be prepared by enzymatic processing of a long, double-stranded RNA having sufficient complementarity to the desired target mRNA. Processing of long RNA can be accomplished in vitro, for example, using appropriate cellular lysates and siRNAs can be subsequently purified by gel electrophoresis or gel filtration. siRNA can than be denatured according to art-recognized methodologies. In an exemplary embodiment, siRNA can be purified from a mixture by extraction with a solvent or resin, precipitation, electrophoresis, chromatography, or a combination thereof. Alternatively, the siRNA may be used with no or a minimum of purification to avoid losses due to sample processing.

Alternatively, the siRNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods EnzynioL 180:51-62). The RNA may be dried for storage or dissolved in an aqueous solution. The solution may contain buffers or salts to inhibit annealing, and/or promote stabilization of the double strands.

Commercially available design tools and kits, such as those available from Ambion, Inc. (Austin, Tex.), and the Whitehead Institute of Biomedical Research at MIT (Cambridge, Mass.) allow for the design and production of siRNA. By way of example, a desired mRNA sequence can be entered into a sequence program that will generate sense and antisense target strand sequences. These sequences can then be entered into a program that determines the sense and antisense siRNA oligonucleotide templates. The programs can also be used to add, e.g., hairpin inserts or T1 promoter primer sequences. Kits also can then be employed to build siRNA expression cassettes.

In various embodiments, siRNAs are synthesized in vivo, in situ, and in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNAs Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNAs from a recombinant construct may be produced by introducing the construct into a zygote, an embryonic stem cell, or another multipotent cell derived from the appropriate organism.

In one embodiment, the target mRNA of the invention specifies the amino acid sequence of at least one protein such as a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ERBB2, ERBB3, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), proteins involved in tumor growth (including vascularization) or in metastatic activity or potential, including cell surface receptors and ligands as well as secreted proteins, cell cycle regulatory, gene regulatory, and apoptosis regulatory proteins, immune response, inflammation, complement, or clotting regulatory proteins.

As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which siRNA and morpholino constructs can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

Further proteins include cyclin dependent kinases, c-myb, c-myc, proliferating cell nuclear antigen (PCNA), transforming growth factor-beta (TGF-beta), and transcription factors nuclear factor kappaB (NF-.kappa.B), E2F, HER-2/neu, PKA, TGF-alpha, EGFR, TGF-beta, IGFIR, P12, MDM2, BRCA, Bcl-2, VEGF, MDR, ferritin, transferrin receptor, IRE, C-fos, HSP27, C-raf and metallothionein genes.

The siRNA employed in the present invention can be directed against the synthesis of one or more proteins. Additionally or alternatively, there can be more than one siRNA directed against a protein, e.g., duplicate siRNA or siRNA that correspond to overlapping or non-overlapping target sequences against the same target protein. Accordingly, in one embodiment two, three, four or any plurality of siRNAs against the same target mRNA can be including in the cochleate compositions of the invention. Additionally, several siRNAs directed against several proteins can be employed. Alternatively, the siRNA can be directed against structural or regulatory RNA molecules that do not code for proteins.

In a preferred aspect of the invention, the target mRNA molecule of the invention specifies the amino acid sequence of a protein associated with a pathological condition. For example, the protein may be a pathogen-associated protein (e.g., a viral protein involved in immunosuppression or immunoavoidance of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e. a protein present in the genome of a cell or organism). In another embodiment, the target mRNA molecule of the invention specifies the amino acid sequence of a heterologous protein expressed in a recombinant cell or a genetically altered organism. In another embodiment, the target mRNA molecule of the invention specifies the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

Accordingly, in one embodiment, the siRNA-cochleate compositions of the present invention can be utilized in studies of mammalian cells to clarify the role of specific structural and catalytic proteins. In another embodiment, they can be used in a therapeutic application to specifically target pathogenic organisms, including fungi, bacteria, and viruses.

Cochleate delivery vehicles are stable lipid-cation precipitates that can be composed of simple, naturally occurring materials, e.g., phosphatidylserine, and calcium. Mixtures of naturally occurring molecules (e.g., soy lipids) and/or synthetic or modified lipids can be utilized.

The cochleate structure provides protection from degradation for associated "encochleated" moieties. Divalent cation concentrations in vivo in serum and mucosal secretions are such that the cochleate structure is maintained. Hence, the majority of cochleate-associated molecules, e.g., cargo moieties, are present in the inner layers of a primarily solid, non-aqueous, stable, impermeable structure. Since the cochleate structure includes a series of solid layers, components within the interior of the cochleate structure remain substantially intact, even though the outer layers of the cochleate may be exposed to harsh environmental conditions or enzymes.

The cochleate interior is primarily free of water and resistant to penetration by oxygen. Oxygen and water are primarily responsible for the decomposition and degradation of molecules which can lead to reduced shelf-life. Accordingly, encochleation should also impart extensive shelf-life stability to encochleated siRNAs.

With respect to storage, cochleates can be stored in cation-containing buffer, or lyophilized or otherwise converted to a powder, and stored at room temperature. If desired, the cochleates also can be reconstituted with liquid prior to administration. Cochleate preparations have been shown to be stable for more than two years at 4° C. in a cation-containing buffer, and at least one year as a lyophilized powder at room temperature.

In one embodiment, the cochleate comprises a negatively charged lipid component and a multivalent cation component.

In one embodiment, the lipid is a mixture of lipids, comprising at least 75% negatively charged lipid. In another embodiment, the lipid includes at least 85% negatively charged lipid. In other embodiments, the lipid includes at least 90%, 95% or even 99% negatively charged lipid. All ranges and values between 60% and 100% negatively charged lipid are meant to be encompassed herein.

The negatively charged lipid can include soy-based lipids. Preferably, the lipid includes phospholipids, such as soy phospholipids (soy-based phospholipids). The negatively charged lipid can include phosphotidyl serine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMPS), dipalmitoyl phosphatidylgycerol (DPPG) and the like.

The lipids can be natural or synthetic. For example, the lipid can include esterified fatty acid acyl chains, or organic chains attached by non-ester linkages such as ether linkages (as described in U.S. Pat. No. 5,956,159), disulfide linkages, and their analogs.

In one embodiment the lipid chains are from about 6 to about 26 carbon atoms, and the lipid chains can be saturated or unsaturated. Fatty acyl lipid chains useful in the present invention include, but are not limited to, n-tetradecanoic, n-hexadecanoic acid, n-octadecanoic acid, n-eicosanoic acid, n-docosanoic acid, n-tetracosanoic acid, n-hexacosanoic acid, cis-9-hexadecenoic acid, cis-9-octadecenoic acid, cis, cis-9,12-octadecedienoic acid, all-cis-9,12,15-octadecetrienoic acid, all-cis-5,8,11,14-eicosatetraenoic acid, all-cis-4,7,10,13,16,19-docosahexaenoic acid, 2,4,6,8-tetramethyl decanoic acid, and lactobacillic acid, and the like.

In some embodiments, pegylated lipid also is included. Pegylated lipid includes lipids covalently linked to polymers of polyethylene glycol (PEG). PEG's are conventionally classified by their molecular weight, thus PEG 6,000 MW, e.g., has a molecular weight of about 6000. Adding pegylated lipid generally will result in an increase of the amount of compound (e.g., peptide, nucleotide, and nutrient) that can be incorporated into the precipitate. An exemplary pegylated lipid is dipalmitoylphosphatidylehtanolamine (DPPE) bearing PEG 5,000 MW.

The siRNA-cochleate compositions of the present invention can be provided in a variety of forms (e.g. powder, liquid, suspension) with or without additional components. Suitable forms and additives, excipients, carriers and the like are described herein.

Morpholino-Cochleate Compositions

The present invention also features encochleated morpholino antisense oligonucleotides (morpholinos) and methods (e.g., research and/or therapeutic methods) for using said morpholino-cochleates. In one aspect, the present invention provides a morpholino-cochleate composition that generally includes a cochleate, and a morpholino associated with the cochleate.

Morpholinos function by an RNase H-independent mechanism and are soluble in aqueous solutions, with most being freely soluble at mM concentrations (typically 10 mg/ml to over 100 mg/ml). Morpholinos have high affinity for RNA and efficiently invade even quite stable secondary structures in mRNAs, which results in effective and predictable targeting essentially anywhere from the 5' cap to about +25 of the protein coding region of mRNAs. Morpholinos are free of significant non-antisense effects while the alternative phosphorothioates are plagued by a host of well-documented non-antisense effects. Morpholinos include a morpholine backbone, which is not recognized by nucleases and therefore is stable in the cell compared to phosphorothioates, which typically are degraded in biological systems in a matter of hours. Consequently, considerably fewer morpholinos are required (approximately 100× less) to achieve similar antisense effects. Morpholinos also are superior to phosphorothioates because targeting is more predictable, the activity in cells is more reliable, and the sequence specificity is superior. Summerton, Biochimica et Biophysica Acta 1489: 141-158 (1999). Morpholinos can be designed and prepared according to known methods. E.g., Summerton and Weller, Antisense and Nucleic Acid Drug Development 7187-195 (1997).

Morpholino oligonucleotides suitable for use in the present invention include antisense morpholino oligonucleotides. The morpholino can be between about 7 and 100 nucleotides long, between 10 and 50, between 20 and 35, and between 15 and 30 nucleotides long. In a preferred embodiment, the morpholino oligonucleotide is between about 18 and about 25 nucleotides long. The oligonucleotides can be 17, 18, 19, 20, 21, 22, 23, 24 or 25 nucleotides long.

The morpholinos of the invention preferably mediate RNA interference against a target gene. That is, preferably, the morpholino has a sequence sufficiently complementary to a target RNA (e.g. mRNA or RNA that can be spliced to produce one or more mRNAs) associated with a target gene to trigger the destruction of the target mRNA by the RNAi machinery or process. The morpholino molecule can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand.

The target mRNA cleavage reaction guided by morpholinos is sequence specific. In general, morpholinos containing a nucleotide sequence identical to a portion of the target gene are preferred for inhibition. However, 100% sequence identity between the morpholino and the target gene is not required to practice the present invention. Sequence variations can be tolerated including those that might be expected due to genetic mutation, strain polymorphism, or evolutionary divergence. For example, morpholino sequences with insertions, deletions, and single point mutations relative to the target sequence have also been found to be effective for inhibition. Alternatively, morpholino sequences with nucleotide analog substitutions or insertions can be effective for inhibition.

Sequence identity may readily be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad Sci. USA 87:2264-68, modified as in Karlin and Altschul (1993) Proc. Natl. Acad. Sci. USA 90:5873. Such an algorithm is incorporated into the BLAST programs (version 2.0) of Altschul, et al. (I 990) J Mol Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the morpholino and the portion of the target RNA is preferred. Alternatively, the morpholino may be defined functionally as a nucleotide sequence (or oligonucleotide sequence) that is capable of hybridizing with a portion of the target mRNA transcript (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 ($\log_{10}$[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold 15 Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about or about equal to 10, 12, 15, 17, 20, 22, 25, 27, 30, 32, 35, 37, 40, 42, 45, 47 or 50 bases.

In one embodiment, the morpholino molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the morpholinos in tissue culture medium.

In another embodiment of the present invention the morpholino molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar modified ribonucleotides, the 2'OH-group is replaced by a group selected from H, OR, R, halo, SH, SR, $NH_2$, NHR, $NR_2$ or $NO_2$, wherein R is C1-C6 alkyl, alkenyl or alkynyl and halo is F, Cl, Br or I.

Nucleotide analogues also include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

RNA may be produced enzymatically or by partial/total organic synthesis, any modified ribonucleotide can be introduced by in vitro enzymatic or organic synthesis. In one embodiment, a morpholino is prepared chemically. Methods of synthesizing RNA molecules are known in the art, in particular, the chemical synthesis methods as described in Verina and Eckstein (1998), Annul Rev. Biochem. 67:99. In another embodiment, a morpholino is prepared enzymatically. For example, a morpholino can be prepared by enzymatic processing of a long, double-stranded RNA having sufficient complementarity to the desired target mRNA. Processing of long RNA can be accomplished in vitro, for example, using appropriate cellular lysates and morpholinos can be subsequently purified by gel electrophoresis or gel filtration. Morpholinos can then be denatured according to art-recognized methodologies. In an exemplary embodiment, morpholinos can be purified from a mixture by extraction with a solvent or resin, precipitation, electrophoresis, chromatography, or a combination thereof. Alternatively, the morpholino may be used with no or a minimum of purification to avoid losses due to sample processing.

In one embodiment, morpholinos are synthesized either in vivo, in situ, or in vitro. Endogenous RNA polymerase of the cell may mediate transcription in vivo or in situ, or cloned RNA polymerase can be used for transcription in vivo or in vivo. For transcription from a transgene in vivo or an expression construct, a regulatory region (e.g., promoter, enhancer, silencer, splice donor and acceptor, polyadenylation) may be used to transcribe the morpholinos. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses morpholinos from a recombinant construct may be produced by introducing the construct into a zygote, an embryonic stem cell, or another multipotent cell derived from the appropriate organism.

In one embodiment, the target mRNA of the invention specifies the amino acid sequence of at least one protein such as a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ETSI, ETSI, ETV6. FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), proteins involved in tumor growth (including vascularization) or in metastatic activity or potential, including cell surface receptors and ligands as well as secreted proteins, cell cycle regulatory, gene regulatory, and apoptosis regulatory proteins, immune response, inflammation, complement, or clotting regulatory proteins.

As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which siRNA and morpholino constructs can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

Further proteins include cyclin dependent kinases, c-myb, c-myc, proliferating cell nuclear antigen (PCNA), transforming growth factor-beta (TGF-beta), and transcription factors nuclear factor kappaB (NF-.kappa.B), E2F, HER-2/neu, PKA, TGF-alpha, EGFR, TGF-beta, IGFIR, P12, MDM2, BRCA, Bcl-2, VEGF, MDR, ferritin, transferrin receptor, IRE, C-fos, HSP27, C-raf and metallothionein genes.

The morpholinos employed in the present invention can be directed against the synthesis of one or more proteins. Additionally or alternatively, there can be more than one morpholino directed against a protein, e.g., duplicate morpholinos or morpholinos that correspond to overlapping or non-overlapping target sequences against the same target protein. Additionally, several morpholinos directed against several proteins can be employed. Accordingly, in one embodiment two, three, four or any plurality of morpholinos against the same target mRNA can be including in the cochleate compositions of the invention. Alternatively, the morpholino can be directed against structural or regulatory RNA molecules that do not code for proteins.

In a preferred aspect of the invention, the target mRNA molecule of the invention specifies the amino acid sequence of a protein associated with a pathological condition. For example, the protein may be a pathogen-associated protein (e.g., a viral protein involved in immunosuppression or immunoavoidance of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e. a protein present in the genome of a cell or organism). In another embodiment, the target mRNA molecule of the invention specifies the amino acid sequence of a heterologous protein expressed in a recombinant cell or a genetically altered organism. In another embodiment, the target mRNA molecule of the invention specifies the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

Accordingly, in one embodiment, the morpholino-cochleate compositions of the present invention can be utilized in studies of mammalian cells to clarify the role of specific structural and catalytic proteins. In another embodiment, they can be used in a therapeutic application to specifically target pathogenic organisms, including fungi, bacteria, and viruses.

Cochleate delivery vehicles are stable lipid-cation precipitates that can be composed of simple, naturally occurring materials, e.g., phosphatidylserine, and calcium. Mixtures of naturally occurring molecules (e.g., soy lipids) and/or synthetic or modified lipids can be utilized.

The cochleate structure provides protection from degradation for associated "encochleated" moieties. Divalent cation concentrations in vivo in serum and mucosal secretions are such that the cochleate structure is maintained. Hence, the majority of cochleate-associated molecules, e.g., cargo moieties, are present in the inner layers of a primarily solid, non-aqueous, stable, impermeable structure. Since the cochleate structure includes a series of solid layers, components within the interior of the cochleate structure remain substantially intact, even though the outer layers of the cochleate may be exposed to harsh environmental conditions or enzymes.

The cochleate interior is primarily free of water and resistant to penetration by oxygen. Oxygen and water are primarily responsible for the decomposition and degradation of molecules which can lead to reduced shelf-life. Accordingly, encochleation should also impart extensive shelf-life stability to encochleated morpholinos.

With respect to storage, cochleates can be stored in cation-containing buffer, or lyophilized or otherwise converted to a powder, and stored at room temperature. If desired, the cochleates also can be reconstituted with liquid prior to administration. Cochleate preparations have been shown to be stable for more than two years at 4° C. in a cation-containing buffer, and at least one year as a lyophilized powder at room temperature.

In one embodiment, the cochleate comprises a negatively charged lipid component and a multivalent cation component.

In one embodiment, the lipid is a mixture of lipids, comprising at least 75% negatively charged lipid. In another embodiment, the lipid includes at least 85% negatively charged lipid. In other embodiments, the lipid includes at least 90%, 95% or even 99% negatively charged lipid. All ranges and values between 60% and 100% negatively charged lipid are meant to be encompassed herein.

The negatively charged lipid can include soy-based lipids. Preferably, the lipid includes phospholipids, such as soy phospholipids (soy-based phospholipids). The negatively charged lipid can include phosphotidyl serine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMPS), dipalmitoyl phosphatidylglycerol (DPPG) and the like.

The lipids can be natural or synthetic. For example, the lipid can include esterified fatty acid acyl chains, or organic chains attached by non-ester linkages such as ether linkages (as described in U.S. Pat. No. 5,956,159), disulfide linkages, and their analogs.

In one embodiment the lipid chains are from about 6 to about 26 carbon atoms, and the lipid chains can be saturated or unsaturated. Fatty acyl lipid chains useful in the present invention include, but are not limited to, n-tetradecanoic, n-hexadecanoic acid, n-octadecanoic acid, n-eicosanoic acid, n-docosanoic acid, n-tetracosanoic acid, n-hexacosanoic acid, cis-9-hexadecenoic acid, cis-9-octadecenoic acid, cis, cis-9,12-octadecedienoic acid, all-cis-9,12,15-octadecetrienoic acid, all-cis-5,8,11,14-eicosatetraenoic acid, all-cis-4,7,10,13,16,19-docosahexaenoic acid, 2,4,6,8-tetramethyl decanoic acid, and lactobacillic acid, and the like.

In some embodiments, pegylated lipid also is included. Pegylated lipid includes lipids covalently linked to polymers of polyethylene glycol (PEG). PEG's are conventionally classified by their molecular weight, thus PEG 6,000 MW, e.g., has a molecular weight of about 6000. Adding pegylated lipid generally will result in an increase of the amount of compound (e.g., peptide, nucleotide, and nutrient) that can be incorporated into the precipitate. An exemplary pegylated lipid is dipalmitoylphosphatidylehtanolamine (DPPE) bearing PEG 5,000 MW.

The morpholino-cochleate compositions of the present invention can be provided in a variety of forms (e.g. powder, liquid, suspension) with or without additional components. Suitable forms and additives, excipients, carriers and the like are described herein.

Aggregation Inhibitors

The cochleates and cochleate compositions of the present invention can optionally include an aggregation inhibitor. Aggregation inhibitors work in part by modifying the surface characteristics of the cochleates such that aggregation is inhibited. Aggregation can be inhibited, for example, by steric bulk and/or a change in the nature of the cochleate structure, e.g., a change in the surface hydrophobicity and/or surface charge.

Aggregation can be inhibited and even reversed, and individual cochleate particles can be stabilized by changing the surface properties of the cochleates and thereby inhibiting cochleate-cochleate interaction. Aggregation can be inhibited by including in the liposome suspension a material that prevents liposome-liposome interaction at the time of calcium addition and thereafter. Alternatively, the aggregation inhibitor can be added after formation of cochleates. Additionally, the amount of aggregation inhibitor can be varied, thus allowing modulation of the size of the cochleates.

In one embodiment, the aggregation inhibitor can be employed to achieve cochleates that are significantly smaller and have narrower particle size distributions than compositions without aggregation inhibitors. Such compositions are advantageous for several reasons including that they can allow for greater uptake by cells, and rapid efficacy. Such a composition is suitable, e.g., when it is desired to rapidly and effectively deliver encochleated molecules. Moreover, cochleate size can have a targeting affect in that some cells may take up particles of a certain size more or less effectively. Size may also affect the manner in which cochleates interact with a cell (e.g., fusion events or uptake).

In another embodiment, the aggregation inhibitor can be employed to achieve cochleate compositions having a particle size relatively larger than that which can be achieved with or without aggregation inhibitors. Such a composition can be useful, e.g., when delayed uptake and/or release of encochleated molecules is desired, or when targeted cells or organs more effectively take up cochleates in the relatively larger size range. Such compositions also may have sustained activity (relative to smaller cochleate compositions) because it can take longer for the molecule to be released from a larger cochleate, e.g., if multiple fusion events are required.

In yet another embodiment, the cochleate composition has a wide particle size distribution such that the encochleate molecule (e.g., siRNA or morpholino and any additional cargo moeity) is released over a period of time because smaller cochleates are rapidly taken up initially followed by take up or fusion events with increasingly larger cochleates. In addition, size may not only affect what type of cells take up the cochleates, but also how the cochleates interact with certain cells, e.g., size may effect whether a cochleate is taken up by a cell or undergoes one or more fusion events with a cell.

Moreover, in yet further embodiments, several compositions can be combined for desired release profiles, e.g., a pulsed released, or combined release. For example, a rapid release nanocochleate composition can be mixed with a delayed-release larger size or even standard cochleate composition, such that an immediate and a delayed release is realized. In addition, the cochleate compositions may have different siRNAs or morpholinos.

An aggregation inhibitor also can be employed to stabilize particle size and particle size distribution. For example, it can be used to "lock-in" the cochleate size and distribution of standard cochleates and/or cochleates having an aggregation inhibitor. While the cochleates of the invention typically are stable over long periods of time, standard cochleates (cochleates formed without aggregation inhibitors) can tend to aggregate over time. Thus, standard cochleates can be stabilized by addition to such aggregation inhibitors, e.g., addition of methylcellulose after cochleate formation.

Accordingly, in one embodiment, cochleate compositions of the invention have a mean diameter less than about 1 micrometer, e.g., less than about 900 nm, 800 nm, 700 nm, 600 nm, 500 nm, 400 nm, 300 nm, 200 nm, 100 nm, 50 nm, 10 nm, or 1 nm. All individual values and ranges within these ranges are meant to be included and are within the scope of this invention. In another embodiment, cochleate compositions of the invention have a mean diameter about equal to or greater than about 1 micrometer, e.g., 2, 3, 4, 5, 10, 50, or 100 micrometers. All individual values and ranges within these ranges are meant to be included and are within the scope of this invention.

In one embodiment, the size distribution is narrow relative to that observed in standard cochleates (cochleates formed without aggregation inhibitors). Preferably, the cochleate compositions have a size distribution of less than about 1 μm, 900 nm, 800 nm, 700 nm, 600 nm, 500 nm, 400 nm, 300 nm, 200 nm, or 100 nm. All individual values between these values (550 nm, 420 nm, 475 nm, etc.), are meant to be included and are within the scope of this invention. Such cochleate compositions are particularly desirable where uptake by macrophages is desired. It can readily be appreciated that particle size can be adjusted to a size suitable for uptake by desired organs or cells and/or unsuitable for uptake by organs or cells. In another embodiment, a wider size distribution of cochleates is employed, e.g., about 10, 20, 50, 100, 200, 300, 400 or 500 micrometers. All individual values within these ranges are meant to be included and are within the scope of this invention. Such cochleate compositions can be useful for long term release of cargo moieties.

Additionally, as discussed above, the invention contemplates combination of cochleate populations to achieve a desired release pattern, e.g., pulsed release and/or timed release of siRNAs or morpholinos against one or more target mRNAs.

The type and/or amount of aggregation inhibitor used can also determine the size of resulting cochleate. The presence of an aggregation inhibitor in differing concentrations also allows regulation of cochleate size distribution.

Suitable aggregation inhibitors that can be employed in accordance with the present invention, include but are not limited to at least one of the following: casein, K-casein, milk, albumin, serum albumin, bovine serum albumin, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, whey protein isolate and mixtures thereof.

A preferred aggregation inhibitor is casein. Casein is a highly phosphorylated, calcium binding protein. Without wishing to be bound to any particular theory, it is believed that calcium mediates an interaction between negatively charged lipid (e.g., PS) and casein, thereby changing the surface properties of cochleates such that aggregation is inhibited. Another preferred aggregation inhibitor is milk and other milk products such as Half and Half, cream etc. Preferred milk products also contain casein. Another preferred aggregation inhibitor is methylcellulose. In addition, more than one aggregation inhibitor may be employed in the cochleates of the invention. For example, both casein and methylcellulose may be used as an aggregation inhibitor.

In one embodiment, the cochleates of the invention include an aggregation inhibitor to lipid ratio of between about 0.1:1 to about 4:1 by weight. Preferably, the aggregation inhibitor to lipid ratio is about 1:1. A person of ordinary skill in the art will readily be able to determine the amount of aggregation inhibitor needed to form cochleates of the desired size with no more than routine experimentation.

Additional Cargo Moieties

The cochleates and cochleate compositions of the present invention can further include one or more additional cargo moieties. An "additional cargo moiety" is an encochleated moiety in addition to the siRNA or morpholino of the invention, and generally does not refer to the lipid and ion employed to precipitate the cochleate. Cargo moieties include any compounds having a property of biological interest, e.g., ones that have a role in the life processes of a living organism. A cargo moiety may be organic or inorganic, a monomer or a polymer, endogenous to a host organism or not, naturally occurring or synthesized in vitro and the like.

The cargo moiety can be a protonized cargo moiety. The term "protonized cargo moiety" refers to a protonizable cargo moiety that has been protonized. "Protonizable" refers to the ability to gain one or more protons. The protonizable cargo moiety can be weakly basic, and can be protonized by acidification or addition of a proton. Additionally or alternatively, the protonizable cargo moiety can be neutral or weakly acidic and can be protonized in the same manner. Thus, the protonzable cargo moiety can be an anionic or a neutral cargo moiety, which is rendered cationic by protonization, or the protonizable cargo moiety can be cationic, and be rendered more cationic upon protonization. The cargo moiety can also be provided protonized. Optionally, the protonized state can be induced, e.g., by acidification or other methods, as described herein. Acidification renders the cargo moiety cationic or increases the valency of a cargo moiety that is already cationic, e.g., from monovalent to divalent or trivalent.

Exemplary additional cargo moieties include vitamins, minerals, nutrients, micronutrients, amino acids, toxins, microbicides, microbistats, co-factors, enzymes, polypeptides, polypeptide aggregates, polynucleotides, lipids, carbohydrates, nucleotides, starches, pigments, fatty acids, monounsaturated fatty acids, polyunsaturated fatty acids, flavorings, essential oils, extracts, hormones, cytokines, viruses, organelles, steroids and other multi-ring structures, saccharides, metals, metabolic poisons, imaging agents, antigens, porphyrins, tetrapyrrolic pigments, marker compounds, medicaments, drugs and the like.

The cargo moiety can be a diagnostic agent, such as an imaging agent. Imaging agents include nuclear agents and fluorescent probes, e.g., porphyrins. Porphyrins include tetrapyrrolic agents or pigments. One such tetrapyrrolic agent is Zinc Tetra-Phenyl Porphyrin (ZnTPP), which is a hydrophobic, fluorescent molecule that has high absorption in the visible spectrum (dark purple).

The cargo moiety can be a polynucleotide that is expressed to yield a biologically active polypeptide or polynucleotide. Thus, the polypeptide may serve as an immunogen or, e.g., have enzymatic activity. The polynucleotide may have catalytic activity, for example, be a ribosome, or may serve as an inhibitor of transcription or translation, e.g., a small interfering RNA (siRNA) or an antisense molecule. The polynucleotide can be modified, e.g., it can be synthesized to have a morpholino backbone. If expressed, the polynucleotide preferably includes the necessary regulatory elements, such as a promoter, as known in the art. A specific example of a polypeptide is insulin.

The drug can be an organic molecule that is hydrophobic in aqueous media. The drug can also be a water-soluble monovalent or polyvalent cationic molecule, anionic, or net neutral at physiological pH. The drug can be, but is not limited to, a protein, a small peptide, a bioactive polynucleotide, an antibiotic, an antiviral, an anesthetic, an antidepressant, an antipsychotic, an anti-infectious, an antifungal, an anticancer, an immunosuppressant, an immunostimulant, a steroidal anti-inflammatory, a non-steroidal anti-inflammatory, an antioxidant, an antidepressant which can be synthetically or naturally derived, a substance which supports or enhances mental function or inhibits mental deterioration, an anticonvulsant, an HIV protease inhibitor, a non-nucleophilic reverse transcriptase inhibitor, a cytokine, a tranquilizer, mucolytic agent, a dilator, a vasoconstrictor, a decongestant, a leukotriene inhibitor, an anti-cholinergic, an anti-histamine a cholesterol, a lipid metabolism modulating, or a vasodilatory agent.

Examples of additional cargo moieties include Amphotericin B, acyclovir, adriamycin, carbamazepine, ivermectin, melphalen, nifedipine, indomethacin, curcumin, aspirin, ibuprofen, naproxen, acetaminophen, rofecoxib, diclofenac, ketoprofin, meloxicam, nabumetone, estrogens, testosterones, steroids, phenyloin, ergotamines, cannabinoids, rapamycin, propanadid, propofol, alphadione, echinomycin, miconazole nitrate, teniposide, hexamethylmelamine, taxol, taxotere, 18-hydroxydeoxycorticosterone, prednisolone, dexamethazone, cortisone, hydrocortisone, piroxicam, diazepam, verapamil, vancomycin, tobramycin, teicoplanin, bleomycin, peptidolglycan, ristocetin, sialoglycoproteins, orienticin, avaporcin, helevecardin, galacardin, actinoidin, gentamycin, netilmicin, amikacin, kanamycin A, kanamycin B, neomycin, paromomycin, neamine, streptomycin, dihydrostreptomycin, apramycin, ribostamycin, spectinomycin, caspofungin, echinocandin B, aculeacin A, micafungin, anidulafungin, cilofungin, pneumocandin, geldanamycin, nystatin, rifampin, tyrphostin, a glucan synthesis inhibitor, vitamin A acid, mesalamine, risedronate, nitrofurantoin, dantrolene, etidronate, nicotine, amitriptyline, clomipramine, citalopram, dothepin, doxepin, fluoxetine, imipramine, lofepramine, mirtazapine, nortriptyline, paroxetine, reboxitine, sertraline, trazodone, venlafaxine, dopamine, St. John's wort, phosphatidylserine, phosphatidic acid, amastatin, antipain, bestatin, benzamidine, chymostatin, 3,4-dichloroisocoumarin, elastatinal, leupeptin, pepstatin, 1,10-phenanthroline, phosphoramidon, ethosuximide, ethotoin, felbamate, fosphenyloin, lamotrigine, levitiracetam, mephenyloin, methsuximide, oxcarbazepine, phenobarbital, phensuximide, primidone, topirimate, trimethadione, zonisamide, saquinavir, ritonavir, indinavir, nelfinavir, and amprenavir.

Additional drugs include, but are not limited to agents that reduce the risk of atherosclerotic events and/or complications thereof. Such agents include, but are not limited to beta blockers, beta blockers and thiazide diuretic combinations, HMG CoA reductase inhibitors, statins, aspirin, ace inhibitors, ace receptor inhibitors (ARBs), and the like. Suitable beta blockers include, but are not limited to cardioselective (selective beta 1 blockers), e.g., acebutolol (e.g., Sectral™), atenolol (e.g., Tenormin™), betaxolol (e.g., Kerlone™), bisoprolol (e.g., Zebeta™), metoprolol (e.g., Lopressor™), and the like. Suitable non-selective blockers (block beta 1 and beta 2 equally) include, but are not limited to carteolol (e.g., Cartrol™, nadolol (e.g., Corgard™), penbutolol (e.g., Levatol™), pindolol (e.g., Visken™), propranolol (e.g., Inderal™, timolol (e.g., Blockadren™), labetalol (e.g., Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like. Suitable statins include, but are not limited to pravastatin (e.g., Pravachol™), simvastatin (e.g., Zocor™), lovastatin (e.g., Mevacor™), and the like. Suitable ace inhibitors include, but are not limited to captopril (e.g., Capoten™), benazepril (e.g., Lotensin™), enalapril (e.g., Vasotec™, fosinopril (e.g., Monopril™, lisinopril (e.g., Prinivil™ or Zestril™), quinapril (e.g., Accupril™), ramipril (e.g., Altace™), imidapril, perindopril erbumine (e.g., Aceon™), trandolapril (e.g., Mavik™), and the like. Suitable ARBS (Ace Receptor Blockers) include but are not limited to losartan (e.g., Cozaar™), irbesartan (e.g., Avapro™, candesartan (e.g., Atacand™), valsartan (e.g., Diovan™), and the like.

Suitable HMG CoA reductase inhibitors that are useful in accordance with the methods and compositions of the invention are statin molecules. These include: Lovastatin (e.g., Mevacor™), Pravastatin (e.g., Pravachol™), Simvastatin (e.g., Zocor™), Fluvastatin (e.g., Lescol™), Atorvastatin (e.g., Lipitor™), or Cerivastatin (e.g., Baycol™).

Other agents that may be administered in conjunction with the cochleates of the invention for treatment of atherosclerotic events and/or complications thereof are phytosterols, phytostanols and their derivatives and isomers; soy protein; soluble fibers, e.g. beta-glucan from, for example, oat and psyllium, nuts, rice bran oil, each of which is particularly suitable for use in food, dietary supplements and food additive compositions. Phytosterols may be solid (e.g., powder, granules) or liquid (e.g., oil) form.

It will be obvious to a person of skill in the art that the choice of the agent for treatment of atherosclerotic events and/or complications thereof depends on the intended delivery vehicle (e.g., food, supplement, pharmaceutical) and the mode of administration.

The cargo moiety can be a polypeptide such as cyclosporin, Angiotensin I, II and III, enkephalins and their analogs, ACTH, anti-inflammatory peptides I, II, III, bradykinin, calcitonin, b-endorphin, dinorphin, leucokinin, leutinizing hormone releasing hormone (LHRH), insulin, neurokinins, somatostatin, substance P, thyroid releasing hormone (TRH) and vasopressin.

The cargo moiety can be an antigen, but is not limited to a protein antigen. The antigen can also be a carbohydrate or DNA. Examples of antigenic proteins include membrane proteins, envelope glycoproteins from viruses, animal cell proteins, other viral proteins, plant cell proteins, bacterial proteins, and parasitic proteins.

Suitable nutrients include, but are not limited to lycopene, micronutrients such as phytochemicals or zoochemicals, vitamins, minerals, fatty acids, amino acids, fish oils, fish oil extracts, biotin, choline, inositol, ginko, and saccharides, herbal products or essential oils. Specific examples include Vitamins A, B, B1, B2, B3, B12, B6, B-complex, C, D, E, and K, vitamin precursors, caroteniods, and beta-carotene, resveratrol, lutein, zeaxanthine, quercetin, silibinin, perillyl alcohol, genistein, sulfurophane, and essential fatty acids, including eicosapentanoic acid (EPA), gamma-3, omega-3, gamma-6, and omega-6 fatty acids, herbs, spices, and iron. Minerals include, but are not limited to boron, chromium, colloidal minerals, colloidal silver, copper, manganese, potassium, selenium, vanadium, vanadyl sulfate, calcium, magnesium, barium, iron and zinc.

The cargo moiety can be a saccharide or sweetener, e.g., saccharine, isomalt, maltodextrine, aspartame, glucose, maltose, dextrose, fructose and sucrose. Flavor agents include oils, essential oils, or extracts, including but not limited to oils and extracts of cinnamon, vanilla, almond, peppermint, spearmint, chamomile, geranium, ginger, grapefruit, hyssop, jasmine, lavender, lemon, lemongrass, marjoram, lime, nutmeg, orange, rosemary, sage, rose, thyme, anise, basil, and black pepper, tea or tea extracts, an herb, a citrus, a spice or a seed.

As used herein, the term "fragile nutrients" refers to fragile compounds (e.g., susceptible to degradation by oxygen, water and the like) derived from plant sources (phytochemicals), animal sources (zoochemicals), or synthetic sources that are either known or are suspected of contributing to the health of an animal.

As used herein, "micronutrient" is a nutrient that the body must obtain from outside sources. Generally micronutrients are essential to the body in small amounts.

In one embodiment, the cargo moiety is added to the composition in a lipid to cargo moiety ratio from between about 20,000:1 to about 1:1. Preferably the cargo moiety is loaded in a lipid to cargo moiety ratio from about 10:1 to about 1:1. More preferably, the cargo moiety is loaded in a lipid to cargo moiety ratio of about 5:1. In another embodiment, a second cargo moiety is additionally incorporated into the cochleate structure in a lipid to cargo moiety ratio of between about 20,000:1 to about 1:1. Preferably the second cargo moiety is loaded in a lipid to cargo moiety ratio from about 10:1 to about 1:1. More preferably, the second cargo moiety is loaded in a lipid to cargo moiety ratio of about 5:1.

Methods of Manufacture

In another aspect, the present invention generally is directed to methods of making cochleates that include siRNA and/or morpholinos. The methods generally can include precipitating a liposome suspension in the presence of an siRNA component and/or a morpholino component, e.g., by adding a multivalent cation. The cochleates can further include additional cargo moieties or other constituents, e.g., aggregation inhibitors. All of the methods described herein can be employed for making both morpholino-cochleates and siRNA cochleates.

Liposomes may be prepared by any known method of preparing liposomes. Thus, the liposomes may be prepared for example by solvent injection, lipid hydration, reverse evaporation, freeze drying by repeated freezing and thawing. The liposomes may be multilamellar or unilamellar, including small unilamellar vesicles (SUV). The liposomes may be large unilamellar vesicles (LUV), stable plurilamellar vesicles (SPLV) or oligolamellar vesicles (OLV) prepared, e.g., by detergent removal using dialysis, column chromatography, bio beads SM-2, by reverse phase evaporation (REV), or by formation of intermediate size unilamellar vesicles by high pressure extrusion. Methods in Biochemical Analysis, 33:337 (1988). Liposomes made by all these and other methods known in the art can be used in practicing this invention.

In a preferred embodiment at least majority of the liposomes are unilamellar. The method can further include the step of filtering a liposomal suspension and/or mechanically extruding the suspension through a small aperture that includes both MLV and ULV liposomes, such that a majority of the liposomes are ULV. In preferred embodiments, at least 70%, 80%, 90% or 95% of the liposomes are ULV.

The method is not limited by the method of forming cochleates. Any known method can be used to form cochleates from the liposomes of the invention (i.e., the liposomes associated with the cargo moiety). In one embodiment, known methods can be employed to form the cochleates of the invention, including but not limited to those described in U.S. Pat. Nos. 5,994,318 and 6,153,217, the entire disclosures of which are incorporated herein by this reference.

In one embodiment, prior to precipitation, SUVs are obtained by, e.g., filtration, and the liposomes are precipated in the presence of siRNA, morpholinos and/or other cargo moiety to form cochleates.

In another embodiment, MLVs are extruded one or more times in the presence of siRNA, morpholinos and/or other cargo moiety, then the liposomes are precipitated form cochleates. In this embodiment, it is believed that the MLVs open and reseal during the extrusion process thereby entrapping or otherwise increasing the association of the siRNA, morpholinos and/or other cargo moieties with the MLVs.

In yet another embodiment, a chelating agent (e.g., EDTA) is employed to convert cochleates to liposomes in the presence of the siRNA or morpholino and/or other cargo moiety, and then cation is added to form the cochleates.

In yet another embodiment, enhanced binding of the siRNA or morpholino and the liposome and/or cochleates is achieved by first forming a complex between the siRNA or morpholino and a transfection agent. Such a cationic transfection agent is preferably a polycation, e.g., polyethylenimine (PEI), polyvinylamine, spermine, spermidine, histamine, cationic lipid, or other moiety to enhance binding to the liposome prior to precipitation. Alternatively the polycation is mixed with and binds to the liposome first and then the RNA or morpholino is added. The high transfection potential of DNA complexed with the cationic polymer polyethylenimine (PEI) has been described. Boussif et al. Proc Natl Acad Sci USA 92: 7297-7301 (1995). However, increased transfection rates have been coupled with increased toxicity. Bogdan et al., AAPS PharmSci 4(2) (2002). PEI can be obtained, e.g., from BASF, such as that sold under the tradename Lupasol G35. Cationic polymers may be employed having a variety of molecular weights, and may be branched or unbranched.

It has been discovered, and illustrated the Examples provided herein, that encochleated siRNA-PEI complexes improve transfection into cells without the associated toxicity observed in the literature and in the Examples. In preferred embodiments the cation is a cationic polymer, e.g., PEI or PEI derivatives. Such complexes can be associated with the liposomes by any of the methods discussed herein.

The ratios of lipid to siRNA, and PEI to siRNA, etc. may vary. In a preferred embodiment, N to P ratios (N, nitrogen in PEI to P, phosphate in RNA) may vary from between about 0.5 to about 20. Most preferably between about 4 to about 8.

Additionally or alternatively, siRNA or morpholinos can be encochleated with high or low amounts of calcium. Accordingly, in one embodiment, a high or "elevated" amount of calcium is used, e.g., wherein the calcium concentration in the solution when the cochleates are formed is between about 100 and about 500 mMolar. As used herein, the term "elevated amount of calcium" means a calcium concentration between about 100 and about 500 mMolar. In another embodiment, a relatively low ("depressed") amount of calcium is used, e.g., between about 1 to about 10 mM. As used herein, the term "depressed amount of calcium" means a calcium concentration between about 1 and about 10 mM. As demonstrated in the examples, siRNA encochleated with high amounts of calcium were more active than siRNA encochleated with low amounts of calcium.

In one embodiment, the pH of the morpholino or siRNA is adjusted in order to induce a charge in the molecule and thereby increase its interaction with the cochleate, and in particular the phospholipid. In one embodiment, the method includes adjusting the pH of the liposomal suspension. In another embodiment, the method may include charging the base pairs of the siRNA or morpholino. For example, the pH can be adjusted to about 8.5 or about 6.0 to 6.5 or about 3.0 to 3.5 for a morpholino. Raising the pH of a liposomal suspension in the presence of morpholino causes the morpholino to associate or complex with the liposomes. Raising or lowering the pH of the siRNA or morpholino (between 3 to 11) can affect charge on the bases or backbone and enhance association with the lipid.

It has been discovered that adjusting the pH and/or charging the base pairs can improve association of the morpholino or siRNA with the cochleate. Accordingly, the method can further include the step of adjusting the pH of the morpholino or siRNA prior to or during the contact with the liposome or formation of the precipitate. Any known method of adjusting pH can be employed. For example, a morpholino or siRNA can be acidified with acidic aqueous buffer. Alternately, pH can be raised with a basic aqueous buffer. Acidic and basic buffers are known in the art, and identification of a variety of buffers would require no more than routine experimentation by one of ordinary skill in the art. Alternatively, the pH of the morpholino or siRNA can be adjusted by slow addition of an acid, e.g., hydrochloric acid, or a base, e.g., sodium hydroxide.

In yet other embodiments, the pH of the morpholinos or siRNA can be adjusted prior to incorporation into the lipid precipitates. In other embodiments, the pH of the resultant morpholino cochleates in solution can be adjusted using, e.g., acid or base.

In one embodiment, cochleates may be formed by dissolving a lipid component and siRNA, morpholino and/or other cargo moiety in an organic solvent (e.g., THF) to form a solution, forming cargo moiety liposomes, and precipitating the liposome to form a cargo moiety-cochleate. The solvent can optionally be removed prior to the formation of liposomes and/or after the liposomes are formed.

In another embodiment, cochleates can be formed by introducing the molecule (e.g, siRNA, morpholino and/or additional cargo moiety), to a liposome in the presence of a solvent such that the molecule associate with the liposome, and precipitating the liposome to form a cochleate. The molecule can be introduced by introducing a solution of the solvent and the molecule to the liposome by, e.g., dropwise addition, continuous flow or as a bolus. The molecule can also be introduced to the liposome prior to or after the solvent.

The liposome may be prepared by any known method of preparing liposomes. Additionally, the method is not limited by the method of forming cochleates. Any known method can be used to form cochleates from the liposomes of the invention (i.e., the liposomes associated with the cargo moiety). In a preferred embodiment, the cochleate is formed by precipitation. Additionally or alternatively, an aggregation inhibitor can be added to the solvent at the liposomal stage, or to the precipitated cochleate.

Any suitable solvent can be employed in connection with the present invention. Solvents suitable for a given application can be readily identified by a person of skill in the art. Suitable solvents include but are not limited to dimethylsulfoxide (DMSO), a methylpyrrolidone, N-methylpyrrolidone (NMP), acetonitrile, alcohols, e.g., butanol and ethanol (EtOH), dimethylformamide (DMF), tetrahydrofuran (THF), and combinations thereof.

Moreover, the order of addition of various components (e.g., siRNA, lipid, calcium, cation complexing agents, solvent) can readily be varied as exemplified in the Examples provided in the instant application. Concentrations and ratios of various components can also be modified as exemplified herein. Finally, ionic conditions may be adjusted as appropriate. Salt concentrations may be approximately isotonic (150 mM), to high (e.g., 1 to 2 molar), to hypotonic, to zero (water).

An exemplary method of forming morpholino-cochleates in accordance with the present invention can generally include the following steps. Liposomes and morpholino oligonucleotides can be solubilized and vortexed to form a morpholino-liposome suspension. Typically, about 2 minutes of vortexing is sufficient to form a suitable suspension, which can be varied and confirmed by visual inspection, e.g., through a microscope.

Next, the pH of the suspension is either raised to about 8.5 (e.g., with 1N NaOH) or lowered to about 6.5 (e.g., with 1N HCl). Since the morpholinos are non-charged, this step is done to place a charge on the base pairs of the morpholino, to favor an interaction with the liposomes. This ionic interaction can be achieved by either increasing the pH to 8.5 or by lowering the pH to 6.5. At this point the morpholinos interact with the lipid. The suspension is again vortexed to induce interaction between the morpholinos and the liposomes. Typically, about 10 minutes of vortexing is suitable. Interaction between the morpholinos and the liposomes can be confirmed by phase and defraction microscopy. The morpholinos associate with or incorporate into the liposomal bilayer. The morpholino-liposomes are then filtered (e.g., using a 0.22 micrometer syringe filter).

Calcium solution is added to the suspension with vortexing. A suitable addition technique is to use an eppendorf repeater pipetter with a 500 microliter tip, and to add 10 microliter aliquots to the tube every 10 seconds until cochleates are formed. Cochleate formation can be confirmed, e.g., by observing the preparation under a microscope and by a measurement of pH. The cochleates can then be stably stored at 4° C. in a nitrogen atmosphere.

Methods of Use

In another aspect, the invention provides methods of administering siRNA or morpholinos to a host (e.g. a cell or organism). The method generally includes administering a biologically effective amount of a siRNA-cochleate or morpholino-cochleate composition to a host. The cochleate compositions can include any of the compositions described herein including, e.g., compositions with additional cargo moieties and/or aggregation inhibitors.

The host can be a cell, a cell culture, an organ, a tissue, and organism, an animal etc. For example, in one embodiment, the siRNA or morpholino is delivered to a cell in the host (e.g., to a cytosol compartment of the cell).

In one embodiment the siRNA mediates RNAi against a target mRNA in the host. In another embodiments, the morpholino mediates translation of a target mRNA in the host. In either embodiment, although acting by a different mechanism, specific target protein synthesis preferably is reduced in the host. In preferred embodiments, target protein synthesis is reduced by at least about 10%, 20%, 30%, 40%, 50%, 60%, 70%, 80%, 90%, or even 100%.

Physical methods of introducing siRNAs and morpholinos to cells and organisms employing cochleates include contacting the cells with the cochleates or administering the cochleates to the organism by any means, e.g., orally, intramuscularly, intradermally, transdermally, intranasally, intrarectally, subcutaneously, topically, or intravenously.

siRNA-cochleates and morpholino-cochleates may be directly introduced to or into a cell (i.e., intracellularly), or introduced extracellularly into a cavity, interstitial space, into the circulation of an organism, introduced orally, or may be introduced by bathing a cell or organism in a solution containing the cochleates. Vascular or extravascular circulation, the blood or lymph system, and the cerebrospinal fluid are sites where the cochleate compositions of the present invention may be introduced.

One mechanism by which the siRNA, morpholinos and/or other cargo moieties may be introduced to a cell is via a fusion event between the cochleate and the cell. Many naturally occurring membrane fusion events involve the interaction of calcium with negatively charged phospholipids (e.g., PS and phosphatidylglycerol). Calcium-induced perturbations of membranes containing negatively charged lipids, and the subsequent membrane fusion events, are important mechanisms in many natural membrane fusion processes. Therefore, cochleates can be envisioned as membrane fusion intermediates. As the calcium rich, highly ordered membrane of a cochleate first comes into close approximation to a natural membrane, a perturbation and reordering of the cell membrane is induced, resulting in a fusion event between the outer layer of the cochleate and the cell membrane. This fusion results in the delivery of a small amount of the material associated with the cochleate into the cytoplasm of the target cell. The cochleate can then break free of the cell and be available for another fusion event, either with the same or another cell.

Additionally or alternatively, particularly with active phagocytic cells, cochleates may be taken up by endocytosis and fuse from within the endocytic vesicle. Cochleates made with trace amounts of fluorescent lipids have been shown to bind and gradually transfer lipids to the plasma membrane and interior membranes of white blood cells in vitro. Accordingly, the encochleated siRNA, morpholinos and/or additional cargo moieties of the invention can be introduced to a cell in a host by endocytosis. Alternatively they may be introduced by pinocytosis.

A cell or tissue with a target mRNA may be derived from or contained in any organism. The organism may be a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include *arabidopsis*; field crops (e.g., alfalfa, barley, bean, corn, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber). Examples of vertebrate animals include fish, mammal, cattle, goat, pig, sheep, rodent, hamster, mouse, rat, primate, and human; invertebrate animals include nematodes, other worms, *drosophila*, and other insects.

The cell having the target mRNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, ostcoblasts, osteoclasts, hepatocytes, and cells of the endocrine or exocrine glands.

Depending on the particular target mRNA and the dose of siRNA and/or morpholino material delivered, this process may provide partial or complete loss of function for the target mRNA in a host. A reduction or loss of mRNA expression in at least 20%, 30%, 40%, 50%, 60%, 70%, 80%, 90%, 95% or 99% or more of the host or targeted cells in the host is exemplary. Inhibition of mRNA expression refers to the absence (or observable decrease) in the level of protein and/or mRNA product from a target mRNA. Specificity refers to the ability to inhibit the target mRNA without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

A simple assay that can be employed for assessing siRNA delivery and activity in a variety of compositions follows, many variations on which can readily be ascertained by the skilled practitioner. anti-GFP siRNA and non-specific siRNA can be obtained from commercial sources, e.g., Ambion, Inc (Austin, Tx). Anti-GFP siRNA and non-specific siRNA compositions, e.g., various cochleate compositions described herein or known in the art can be manufactured. Cells, such as SKOV cells can be transfected with green fluorescent protein (GFP) expressing plasmid, followed by treatment with anti-GFP siRNA and non-specific siRNA compositions and any other suitable controls. GFP fluorescence can then be measured after a predetermined time period, e.g., 48 or 72 hours. This data can then be compared to determine which compositions were more effective at delivery of active siRNA than others.

For RNA-mediated inhibition in a cell line or whole organism, mRNA expression is conveniently assayed by use of a reporter or drug resistance mRNA whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of mRNA expression allows one to determine a degree of inhibition which is greater than 10%, 33%, 50%, 90%, 95% or 99% as compared to a cell not treated according to the present invention. Lower doses of injected material and longer times after administration of encochleated siRNA and/or morpholinos may result in inhibition in a smaller fraction of cells (e.g., at least 10%, 20%, 50%, 75%, 90%, or 95% of targeted cells). Quantitation of mRNA expression in a cell may show similar amounts of inhibition at the level of accumulation of target mRNA or translation of target protein.

As an example, the efficiency of inhibition may be determined by assessing the amount of mRNA product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

The cochleates can be coadministered with a further agent. The second agent can be delivered in the same cochleate preparation, in a separate cochleate preparation mixed with the cochleates preparation of the invention, separately in another form (e.g., capsules or pills), or in a carrier with the cochleate preparation. The cochleates can further include one or more additional cargo moieties, such as other drugs, peptides, nucleotides (e.g., DNA and RNA), antigens, nutrients, flavors and/or proteins. Such molecules have been described in U.S. Pat. No. 6,153,217 (Jin et al.) and U.S. Pat. No. 5,994,318 (Gould-Fogerite et al.), and International Patent Publication Nos. WO 00/42989 (Zarif et al.) and WO 01/52817 (Zarif et al.). These patents are expressly incorporated by this reference.

The cochleates of the invention also can include a reporter molecule for use in in vitro diagnostic assays, which can be a fluorophore, radiolabel or imaging agent. The cochleates can include molecules that direct binding of the cochleate to a specific cellular target, or promotes selective entry into a particular cell type.

Another advantage of the present invention is the ability to modulate cochleate size. Modulation of the size of cochleates can change the manner in which the siRNA, morpholino and/or additional cargo moiety is taken up by cells. For example, in general, small cochleates are taken up quickly and efficiently into cells, whereas larger cochleates are taken up more slowly, but tend to retain efficacy for a longer period of time. Also, in some cases small cochleates are more effective than large cochleates in certain cells, while in other cells large cochleates are more effective than small cochleates.

Methods of Treatment

In another aspect, the present invention provides for both prophylactic and therapeutic methods of treating a subject at risk of (or susceptible to) a disorder or having a disorder associated with aberrant or unwanted target gene expression or activity. The method generally includes administering to a subject a therapeutically effective amount of a morpholino-cochleate composition or siRNA-cochleate of the invention such that the disease or disorder is treated.

The present invention provides a method for treating a subject that would benefit from administration of a composition of the present invention. Any therapeutic indication that would benefit from the cochleate compositions of the present invention can be treated by the methods of the invention. The method includes the step of administering to the subject a composition of the invention, such that the disease or disorder is treated.

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

The language "therapeutically effective amount" is that amount necessary or sufficient to produce a desired physiologic response. The effective amount may vary depending on such factors as the size and weight of the subject, or the particular compound. The effective amount may be determined through consideration of the toxicity and therapeutic efficacy of the compounds by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the $EC_{50}$ (i.e., the concentration of the test composition that achieves a half-maximal response) as determined in cell culture. Such information can be used to more accurately determine useful doses in humans. Levels in plasma may be measured, for example, by high performance liquid chromatography.

1. Prophylactic Methods

In one aspect, the invention provides a method for preventing in a subject, a disease or condition associated with an aberrant or unwanted target gene expression or activity, by administering to the subject a therapeutic agent (e.g., morpholinos, siRNAs or vector or transgene encoding same). Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves administering to a host a composition of the invention that is specific for the target gene or protein (e.g., is specific for the mRNA encoded by said gene or specifying the amino acid sequence of said protein) such that expression or one or more of the activities of target protein is modulated. These modulatory methods can be performed in vivo (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target mRNA polypeptide or nucleic acid molecule Inhibition of target mRNA activity is desirable in situations in which the target mRNA is abnormally unregulated and/or in which decreased target mRNA activity is likely to have a beneficial effect.

One advantage of the cochleates of the present invention is the safety and stability of the composition. Cochleates can be administered orally or by instillation without concern, as well as by the more traditional routes, such as oral, intranasal, intraoculate, intraanal, intravaginal, intrapulmonary, topical, subcutaneous, intradermal, intramuscular, intravenous, subcutaneous, transdermal, systemic, intrathecal (into CSF), and the like. Direct application to mucosal surfaces is an attractive delivery means made possible with cochleates.

The disease or disorder treated in accordance with the present invention can be any disease or disorder that can be treated by the successful administration of siRNAs or morpholinos of the invention. Exemplary diseases and disorders include neurological disorders associated with aberrant or unwanted gene expression such as schizophrenia, obsessive compulsive disorder (OCD), depression and bipolar disorder, Alzheimer's disease, Parkinson's disease, lymphoma, immune-mediated inflammatory disorders, hyperplasia, cancers, cell proliferative disorders, blood coagulation disorders, Dysfibrinogenaemia and hemophilia (A and B), dematological disorders, hyperlipidemia, hyperglycemia, hypercholesterolemia, obesity, acute and chronic leukemias and lymphomas, sarcomas, adenomas, fungal infections, bacterial infections, viral infections, a lysosomal storage disease, Fabry's disease, Gaucher's Disease, Type I Gaucher's Disease, Farber's disease, Niemann-Pick disease (types A and B), globoid cell leukodystrophy (Krabbe's disease), metachromic leukodystrophy, multiple sulfatase deficiency, sulfatidase activator (sap-B) deficiency, sap-C deficiency, $G_{M1}$-gangliosidosis, Tay-Sachs disease, Tay-Sachs B1 variant, Tay-Sachs AB variant, Acid Maltase Deficiency, Mucopolysaccharidosis, Sandhoff's disease, a cancer, an autoimmune disorder, systemic lupus erythematosis, multiple sclerosis, myasthenia gravis, autoimmune hemolytic anemia, autoimmune thrombocytopenia, Grave's disease, allogenic transplant rejection, rheumatoid arthritis, ankylosing spondylitis, psoriasis, scleroderma, carcinomas, epithelial cancers, small cell lung cancer, non-small cell lung cancer, prostate cancer, breast cancer, pancreatic cancer, hepatocellular carcinoma, renal cell carcinoma, biliary cancer, colorectal cancer, ovarian cancer, uterine cancer, melanoma, cervical cancer, testicular cancer, esophageal cancer, gastric cancer, mesothelioma, glioma, glioblastoma, pituitary adenomas, inflammatory diseases, osteoarthritis, atherosclerosis, inflammatory bowel diseases (Crohns and ulcerative colitis), uveitis, eczema, chronic rhinosinusitis, asthma, a hereditary disease, cystic fibrosis, and muscular dystrophy.

The method can also be used for regulating gene expression to promote greater health or quality of life, e.g., to limit cholesterol uptake or regulate lipid metabolism, weight gain, hunger, aging, or growth. Cosmetic effects such as wrinkle reduction, hair growth, pigmentation, or dermatologic disorders may also be treated.

The compositions of the present invention can be used to enhance antiviral defense, transposon silencing, gene regulation, centromeric silencing, and genomic rearrangements. The compositions of the invention can also be used to inhibit expression of other types of RNA, e.g., ribosomal RNA, transfer RNA, and small nuclear RNA.

The siRNA and morpholino cochleate compositions of the present invention can be utilized in any number of gene therapies. One such treatment is for the management of opportunistic fungal infections like *Aspergillus fumigatus*, particularly in immunocompromised patients. Current treatment protocols with existing antifungal agents can still result in mortality rates of 80% in HIV patients or those undergoing cancer-related chemotherapies. However, the targeted disruption of the P-type H+-ATPase, an important plasma membrane enzyme critical to fungal cell physiology, may be an alternate and more effective way to destroy fungi such as *A. fumigatus*. This particular ATPase was cloned and selective small interfering RNA (siRNA) oligonucleotides obtained, which can knockdown the expression of this critical protein, resulting in the death of the fungus. siRNA-cochleates having siRNA targeted to the H+-ATPase of *A. fumigatus* will be delivered using cochleate compositions as described herein.

The essential role of the H+-ATPase in spore germination and multiplication of growing cells provides an opportunity to explore the ability of nanocochleates to efficiently deliver siRNAs targeted to the H+-ATPase of *A. fumigatus*. Given the medical importance of *A. fumigatus* and the paucity of available antifungal compounds, siRNA cochleate compositions have the potential to be effective therapeutic alternatives.

Treatment of Fungal Infections

Opportunistic fungal infections are widespread in cancer, HIV infected and other immunosuppressed individuals, and are a growing concern for the management of such patients. These organisms have become important causes of morbidity and mortality in the immunocompromised (Jarvis, W. R., (1995) Clin Infect Dis. 20(6): 1526-30; Dupont Jarvis, B., et al., (1994) J Med Vet Mycol 32(Suppl 1): 65-77; Bodey, G. P. (1988) J Hosp Infect 11 Suppl A:411-26), and make opportunistic fungal infections a major source of nosocomial disease. Pfaller, M. A. (1995) Clin Infect Dis. 20(6):1525; Pfaller, M. A., et al., (1999) Diagn Microbiol Infect Dis, 33(4): p. 217-22; Pfaller, M. A., et al., (1998) Diagn Microbiol Infect Dis 31(1): 289-96; Pfaller, M. A., et al., (1998) Diagn Microbiol Infect Dis 30(2):121-9; Pfaller, M. A., et al., (1998) J Clin Microbiol, 36(7): 1886-9. The mold *Aspergillus fumigatus* causes a variety of diseases including allergic bronchopulmonary aspergillosis in asthma patients and invasive pulmonary aspergillosis (IPA) in immunocompromised patients. Denning, D. W. (1998) Clin Infect Dis 26(4): 781-803; quiz 804-5; Andriole, V. T. (1993) Clin Infect Dis. 17 Suppl 2: S481-6; Latge, J. P. (1999) Clin Microbiol Rev. 12(2): 310-50. Invasive aspergillosis is a common infection in patients who are immunocompromised, particularly in oncology patients, patients receiving other immunosuppressive therapy, bone marrow transplant patients, and HIV-infected patients. *Aspergillus fumigatus* accounts for 30% of fungal infections among cancer patients and 10 to 25% in leukemia patients (Denning, D. W. (1998) Clin Infect Dis 26(4): 781-803; quiz 804-5). Early diagnosis of invasive fungal infections is critical for successful therapeutic outcome, although such determinations are difficult to achieve. Denning, D. W. (1996) Curr Clin Top Infect Dis. 16: 277-99; Andriole, V. T., (1996) Infect Agents Dis. 5(1): 47-54; Latge, J. P., (1995) Curr Top Med Mycol. 6: 245-81. The spectrum of disease manifestations is determined by a combination of genetic predisposition, host immune system defects, and virulence of the *Aspergillus* species. Amphotericin B is the standard of treatment for severe *Aspergillus* infections (Stevens, D. A. et al., (2000) Clin Infect Dis. 30(4): 696-709.), although mortality in these patients remains high. Latge, J. P., (1999) Microbiol Rev. 12(2): 310-50. In addition, amphotericin B may cause toxicity resulting in severe side effects, including permanent renal insufficiency. Newer compositions, like liposomal suspensions, can reduce toxicity but do not eliminate it. Stevens, D. A. et al., (2000) Clin Infect Dis. 30(4): 696-709; Groll, A. H., et al., (1998) Klin Padiatr, 210(4): 264-73; Leenders, A. C., et al., (1998) Br J Haematol, 103(1): 205-12; Ng, T. T. et al. (1995) Arch Intern Med. 155(10): 1093-8; Robinson, R. F. et al. (1999) J Clin Pharm Ther. 24(4): 249-57. As the incidence of topical and invasive mycoses increases, there is a continuing need to develop more effective therapeutics to deal with opportunistic fungal infections and to better understand the pathogenicity of these organisms.

Plasma Membrane Proton Pump (H+-ATPase)

The plasma membrane of all fungi contains an essential proton pumping ATPase (H+-ATPase) that regulates intracellular pH (Morsomme, P. et al. (2000) Biochim Biophys Acta. 1469(3): 133-57; Serrano, R., (1998) Biochim Biophys. Acta. 947: 1-28), and maintains the electrochemical proton gradient across the plasma membrane, which is necessary for nutrient uptake, including certain essential amino acids, sugars and ions. Serrano, R., (1998) Biochim Biophys. Acta. 947: 1-28. The plasma membrane $H^+$-ATPase has been extensively studied at the biochemical, biophysical and genetic levels (Morsomme, P. et al. (2000) Biochim Biophys Acta. 1469(3): 133-57; Perlin, D. S., et al. (1992) Acta Physiol Scand Suppl. 607: 183-92; Moller, J. V. et al. (1996) Biochim Biophys. Acta. 1286: 1-51.) in model organisms such as *Saccharomyces cerevisiae*. It consists of a single $M_r$~100 kDa polypeptide that is a predominant membrane constituent representing 5-30% of the total membrane protein. Monk, B. C., et al., (1991) J Bacteriol. 173(21): 6826-36. It utilizes energy from ATP hydrolysis to actively pump protons from inside the cell to the outside. The $H^+$-ATPase is a typical Class IIIa P-type ion translocating ATPase that includes the $Na^+,K^+$-ATPase of animal cell plasma membranes, $Ca^{2+}$-ATPases of sarcoplasmic reticulum and red blood cells.

The consensus view of the topology and secondary-structure model for $H^+$-ATPase and other type II P-type ATPases enzyme it that they are organized into three distinct structure-function domains. Zhang, P. et al. (1998) Nature. 392: 835-839. The cytoplasmic domain contains the sites for ATP binding and phosphorylation. The membrane embedded transport region contains ten α-helical transmembrane segments. Transmembrane segments M4, M5 and M6 contain aspartate and glumatate residues important for cation binding and ion translocation. Lutsenko, S. et al. (1995) Biochemistry. 34(48): 15607-13; MacLennan, D. H et al. (1997) J Biol Chem. 272(46): 28815-8.

The gene encoding the fungal $H^+$-ATPase, PMA1, shows extensive amino acid sequence similarity between the various fungal enzymes (51-98%), but less than 30% similarity with its animal cell counterparts. Wach, A., A. et al. (1992) J. Bioenerg. Biomembr., 24: 309-317. The catalytic ATP hydrolysis domain displays the highest level of conservation, although signature sequences are found outside this region as well. Lutsenko, S. et al. (1995) Biochemistry. 34(48): 15607-13. The N and C-termini of the P-type ATPases are highly divergent, as are extracellular loop domains linking transmembrane segments, which contribute regulatory features of each class of ATPase. The divergence of structure on the extracellular face of the bilayer occurs among P-type ATPases with different ion specificities but also in isoforms. It accounts for the differential response of the animal cell $Na^+$, $K^+$-ATPase to cardiac glycosides (Lingrel, J. B. et al. (1994) J. Biol. Chem. 269: 19659-19662) and for the specificity of antiulcer drugs like omeprazole to the gastric $H^+,K^+$-ATPase. Sachs, G., et al. (1995) Annu. Rev. Pharmacol. Toxicol., 35: 277-305. It is this well documented ability to develop drug specificity between P-type ATPase molecules that has contributed to the success of this enzyme family as therapeutic targets, and could facilitate the development of highly specific antifungal drugs.

The plasma membrane $H^+$-ATPase plays a critical role in fungal cell physiology and it is one of the few antifungal targets that have been demonstrated to be essential by gene disruption. Serrano, R. et al. (1986) Nature, 1986. 319: 689-693. The fungal $H^+$-ATPase has attributes that are attractive as a drug discovery target. It is an essential enzyme that is needed for both new growth and stable cell maintenance in the absence of growth. Due to its slow turnover in the membrane (~11 h), it is likely that inhibitors of the $H^+$-ATPase will be fungicidal. Preliminary studies with Ebselen, a model compound that inhibits ATP hydrolysis illustrates its fungicidal properties in *Cryptococcus neoformans*. Soteropoulos, P., et al. (2000) Antimicrob Agents Chemother. 44(9): 2349-55. Several recent reports demonstrate $H^+$-ATPase-mediated antifungal properties from novel reagents including CAN-296, a complex carbohydrate (Ben-Josef, A. M., et al. (2000) Int J Antimicrob Agents. 13(4): 287-95) and NC1175, (3-[3-(4-chlorophenyl)-2-propenoyl]-4-[2-(4-chlorophenyl)vinylene]-1-ethyl-4-piperidinol hydrochloride) a thiol-blocking conjugated styryl ketone that also exhibits antifungal activity against a wide spectrum of pathogenic fungi. Manavathu, E. K., et al. (1999) Antimicrob Agents Chemother, 43(12): 2950-9.

The essential role of the P type, H+-ATPase in fungal cell physiology makes this enzyme a good target model for the efficacy of cochleate nanotechnology to deliver the cochleates of the present invention. Given the medical importance of *Aspergillus fumigatus* infection in immunocompromised individuals, and the paucity of available antifungal compounds, siRNA cochleates have the potential to be an effective therapeutic alternative.

Combination Therapies

The above methods can be employed in the absence of other treatment, or in combination with other treatments. Such treatments can be started prior to, concurrent with, or after the administration of the compositions of the instant invention. Accordingly, the methods of the invention can further include the step of administering a second treatment, such as a second treatment for the disease or disorder or to ameliorate side effects of other treatments. Such second treatment can include, e.g., any treatment directed toward reducing an immune response. Additionally or alternatively, further treatment can include administration of drugs to further treat the disease or to treat a side effect of the disease or other treatments (e.g., anti-nausea drugs).

In one aspect, the invention provides a method for preventing in a subject, a disease or disorder which can be treated with administration of the compositions of the invention. Subjects at risk for a disease or condition which can be treated with the agents mentioned herein can be identified by, for example, any or a combination of diagnostic or prognostic assays known to those skilled in the art. Administration of a prophylactic agent can occur prior to the manifestation of symptoms characteristic of the disease or disorder, such that the disease or disorder is prevented or, alternatively, delayed in its progression.

Pharmaceutical Compositions

The invention pertains to uses of the cochleates of the invention for prophylactic and therapeutic treatments as described infra. Accordingly, the cochleates of the present invention can be incorporated into pharmaceutical compositions suitable for administration. Such compositions typically comprise the cochleates of the invention and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

Cochleates of the present invention readily can be prepared from safe, simple, well-defined, naturally occurring substances, e.g., phosphatidylserine (PS) and calcium. Phosphatidylserine is a natural component of all biological membranes, and is most concentrated in the brain. The phospholipids used can be produced synthetically, or prepared from natural sources. Soy PS is inexpensive, available in large quantities and suitable for use in humans. Additionally, clinical studies indicate that PS is safe and may play a role in the support of mental functions in the aging brain. Unlike many cationic lipids, cochleates (which are composed of anionic lipids) are non-inflammatory and biodegradable. The tolerance in vivo of mice to multiple administrations of cochleates by various routes, including intravenous, intraperitoneal, intranasal and oral, has been evaluated. Multiple administrations of high doses of cochleate compositions to the same animal show no toxicity, and do not result in either the development of an immune response to the cochleate matrix, or any side effects relating to the cochleate vehicle.

The cochleates of the present invention can be administered to animals, including both human and non-human animals. It can be administered to animals, e.g., in animal feed or water.

Wetting agents, emulsifiers and lubricants, such as sodium lauryl sulfate and magnesium stearate, as well as coloring agents, release agents, sweetening, flavoring and perfuming agents, preservatives and antioxidants may also be present in the compositions.

Examples of pharmaceutically acceptable antioxidants, which may also be present in compositions of therapeutic compounds of the invention, include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Compositions of the present invention include those suitable for oral, nasal, topical, transdermal, buccal, sublingual, rectal, vaginal or parenteral administration. The compositions may conveniently be presented in unit dosage form and may be prepared by any methods well known in the art of pharmacy. The amount of active ingredient which may be combined with a carrier material to produce a single dosage form will generally be that amount of the composition which produces a therapeutic effect. Generally, out of 100%, this amount will range from about 1% to about 99% of active ingredient, preferably from about 5% to about 70%, most preferably from about 10% to about 30%.

Methods of preparing these compositions or compositions include the step of bringing into association a composition of the present invention with the carrier and, optionally, one or more accessory ingredients. In general, the compositions are prepared by uniformly and intimately bringing into association a composition of the present invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a composition of the present invention as an active ingredient. A composition of the present invention may also be administered as a bolus, electuary, or paste.

In solid dosage forms of the invention for oral administration (capsules, tablets, pills, dragees, powders, granules, and the like), the cochleates of the present invention are mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres.

They may be sterilized by, for example, filtration through a bacteria-retaining filter, or by incorporating sterilizing agents in the form of sterile solid compositions which may be dissolved in sterile water, or some other sterile injectable medium immediately before use.

These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Compositions of the present invention which are suitable for vaginal administration also include pessaries, tampons, creams, gels, pastes, foams or spray compositions containing such carriers as are known in the art to be appropriate.

Dosage forms for the topical or transdermal administration of a composition of this invention include powders, sprays, ointments, pastes, creams, lotions, gels, solutions, patches and inhalants. The composition may be mixed under sterile conditions with a pharmaceutically acceptable carrier, and with any preservatives, buffers, or propellants which may be required.

The ointments, pastes, creams and gels may contain, in addition to a composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a composition of this invention, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a composition of the present invention to the body. Such dosage forms may be made by dissolving or dispersing the composition in the proper medium. Absorption enhancers may also be used to increase the flux of the composition across the skin. The rate of such flux may be controlled by either providing a rate controlling membrane or dispersing the composition in a polymer matrix or gel.

Ophthalmic compositions, eye ointments, powders, solutions and the like, are also within the scope of this invention.

Pharmaceutical compositions of this invention suitable for parenteral administration comprise a cochleate of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the composition isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the siRNA then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride, in the composition. Prolonged absorption of the injectable compositions can be brought about by including in the composition an agent which delays absorption, for example, aluminum monostearate and gelatin.

Sterile injectable solutions can be prepared by incorporating a composition of the invention in the desired amount in an appropriate solvent with one or a combination of ingredients enumerated above, as necessary, followed by filtered sterilization. Generally, dispersions are prepared by incorporating the composition into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the cochleate compositions of the invention plus any additional desired ingredient from a previously sterile-filtered solution thereof.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release may be controlled. Examples of other biodegradable polymers include poly (orthoesters) and poly(anhydrides). Depot injectable compositions are also prepared by entrapping the cochleates in liposomes or microemulsions which are compatible with body tissue.

Oral compositions generally include an inert diluent or an edible carrier. They can be enclosed in gelatin capsules or compressed into tablets. For the purpose of oral therapeutic administration, the composition can be incorporated with excipients and used in the form of tablets, troches, or capsules. Oral compositions can also be prepared using a fluid carrier for use as a mouthwash, wherein the composition in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the composition. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions of the invention also can be prepared in the form of suppositories (e.g., with conventional suppository bases such as cocoa butter and other glycerides) or retention enemas for rectal delivery.

In one embodiment, the compositions of the invention are prepared with carriers that will protect the composition against rapid elimination from the body, such as a controlled release composition, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. The materials can also be obtained commercially from Alza Corporation and Nova Pharmaceuticals, Inc.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a composition calculated to produce the desired therapeutic effect in association with the pharmaceutical carrier. The specification for the dosage unit forms of the invention are dictated by and directly dependent on the unique characteristics of the composition and the particular therapeutic effect to be achieved, and the limitations inherent in the art of compounding such a composition for the treatment of individuals.

The pharmaceutical compositions can be included in a container, pack, or dispenser together with instructions for administration. The pharmaceutical compositions can be included in a container along with one or more additional compounds or compositions and instructions for use. For example, the invention also provides for packaged pharmaceutical products containing two agents, each of which exerts a therapeutic effect when administered to a subject in need thereof. A pharmaceutical composition may also comprise a third agent, or even more agents yet, wherein the third (and fourth, etc.) agent can be another agent against the disorder, such as a cancer treatment (e.g., an anticancer drug and/or chemotherapy) or an HIV cocktail. In some cases, the individual agents may be packaged in separate containers for sale or delivery to the consumer. The agents of the invention may be supplied in a solution with an appropriate solvent or in a solvent-free form (e.g., lyophilized). Additional components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The present invention also includes packaged pharmaceutical products containing a first agent in combination with (e.g., intermixed with) a second agent. The invention also includes a pharmaceutical product comprising a first agent packaged with instructions for using the first agent in the presence of a second agent or instructions for use of the first agent in a method of the invention. The invention also includes a pharmaceutical product comprising a second or additional agents packaged with instructions for using the second or additional agents in the presence of a first agent or instructions for use of the second or additional agents in a method of the invention. Alternatively, the packaged pharmaceutical product may contain at least one of the agents and the product may be promoted for use with a second agent

EXEMPLIFICATION

The use of antisense oligonucleotides as therapeutic agents has been widely investigated in the past few years. Brantl, S. (2002) Biochim Biophys Acta. 1575 (1-3):15-25; Brent, L. J. N, et al. (2002) Neurosci. 114(2):275-278; Akhtar et al. (1991) Nucleic Acids Res. 19: 5551. Their efficacy is based on their ability to recognize their mRNA target in the cytoplasm and to block gene expression by binding and inactivating selected RNA sequences. While the potential of antisense is widely recognized, limitations such as poor specificity, instability, unpredictable targeting and undesirable non-antisense effects hamper therapeutic use of antisense molecules. In addition, one of the major limiting aspects of this gene regulatory strategy is poor cell penetration. Akhtar et al. (1991) Nucleic Acids Res. 19, 5551.

Intracellular delivery and concentration is necessary for antisense inhibition of gene expression. It is believed that naked oligonucleotides enter the cell via active processes of adsorptive endocytosis and pinocytosis. However, naked antisense oligonucleotides do not appear to penetrate the endosomal barrier and gain access to the cytoplasmic compartment to any great extent. Lebedeva, I. et al. (2001) Annu. Rev. Pharmacol. Toxicol. 4:403-419; Weiss, B. et al. (1997) Neurochem. Int. 31:321-348). Although complexes of antisense oligonucleotides with cationic liposomes have enhanced intracellular delivery, they also have significant cytotoxicity. Their utility in vitro and in vivo has also been limited by their lack of stability in serum and their inflammatory properties.

Compositions of the present invention utilize cochleates to achieve enhanced delivery of morpholino antisense molecules in vitro. The morpholine backbone of these antisense molecules is not recognized by nucleases, and is therefore more stable. Morpholinos function by an RNase H-independent mechanism and are soluble in aqueous solutions, with most being freely soluble at mM concentrations (typically 10 mg/ml to over 100 mg/ml). Nasevicius, A. et al. (2000) Nat. Genet. 26:216-220; Lewis, K. E. et al. (2001) Development 128:3485-3495; Mang'era, K. O. et al. (2001) Eur. J. Nucl. Med. 28:1682-1689; Satou, Y. et al. (2001) Genesis. 30:103-106; Tawk, M. et al. (2002) Genesis. 32:27-31. They are highly effective with predictable targeting. Nasevicius, A. et al. (2000) Nat. Genet 26:216-220; Lewis, K. E. et al. (2001) Development. 128:3485-3495; Mang'era, K. O. et al. (2001) Eur. J. Nucl. Med. 28:1682-1689; Satou, Y. et al. (2001) Genesis. 30:103-106; Tawk, M. et al. (2002) Genesis. 32:27-31.

Example 1

Preparation of Morpholino Cochleates

Rhodamine-labeled phosphatidyl ethanolamine (Rho-PE) liposomes were prepared by adding dioleoylphosphatidylserine (DOPS) and Rho-PE at a ratio of 20:1 (Rho-PE: DOPS) to chloroform at a ratio of 10 mg lipid/ml in a 50 ml sterile tube. The concentration of Rho-PE was approximately 0.1% or 0.01% with respect to the DOPS.

The sample was blown down under nitrogen to form a film. Once dry, the sample was resuspended with TES buffer at a ratio of 10 mg lipid/ml. The liposomes were then passed through a 0.22 μm filter. The homogenous population of rhodamine-labeled liposomes were stored at 4° C. in the absence of light under nitrogen.

Morpholinos were obtained from GeneTools, LLC (Philomath, Oreg.) for the GAPDH antisense sequence 5'ATCCGT-TGACACCGACCTTCACCAT3' (SEQ ID NO.: 1), and GAPDH mismatch sequence 5'ATCCCTTGAGAC-CGAGCTTCTCCAT3' (SEQ ID NO.: 2). These sequences have been used previously to target the first 25 bases of the coding sequence and block GAPDH. They were solubilized by adding 0.834 ml TES [N-tris(hydroxymethyl)methyl-2-aminoethanesulfonic acid] buffer to the original bottle at neutral pH. The morpholino stock was stored in 100 μl aliquots at −20° C. Prior to use, the aliquot must be heated at 65° C. for 5 min to ensure the morpholino hasn't dropped out of solution.

Approximately 400 μl of the fluorescent Rho-PE liposome suspension and about 100 μl of the morpholino solution were added to a sterile glass tube and vortexed thoroughly (approximately 2 minutes). The samples were checked for pH and observed both macro- and microscopically. The samples were observed to include liposomes and morpholino oligomers. The pH of the sample was slowly increased to approximately 8.0-8.5, by addition of 1N NaOH. The sample was then vortexed for about 10 minutes. The suspension was then sonicated for about 2 minutes in a nitrogen gas atmosphere, and filtered using a 0.22 μm syringe filter. Morpholinos are hydrophilic non-charged molecules, and therefore do not interact strongly with the liposomes. Raising the pH places a charge on the base pairs of the morpholino, favoring an interaction with the liposomes.

Cochleates were then formed by the slow addition (10 μl) of 0.1M calcium chloride to the suspension of Rho-PE liposomes and morpholino oligomers at a molar ratio of lipid to calcium of 2:1 with an external excess of 6 mM calcium. The calcium chloride was added while vortexing using an eppendorf repeater pipette with a 500 microliter tip, adding 10 μl aliquots to the suspension every 10 seconds. At this point, the sample was observed to include morpholino-cochleates. The sample was then stored at 4° C. in the absence of light.

Samples were also prepared by lowering the pH to approximately 6.0-6.5 as described above. As the pH was decreased from 7.4 to approximately 6.0, an interaction was observed between the lipid and the morpholino, similar to that observed at pH 8.5.

Example 2

Delivery of Morpholinos Via Cochleates into Cells

Morpholino-cochleates were prepared as described in Example 1, with FITC-labeled GAPDH morpholinos. These morpholino-cochleates were administered to NGF differentiated rat P12 cells and photographed at 3 hours and 12 hours as shown in FIGS. 1A and 1B, respectively, after cochleate introduction. As illuminated by the fluoresced rhodamine using LCSM fluorescence imaging, the cochleates fuse with the outer membrane and form submembrane aggregates. FIGS. 1C (low power) and 1D (high power) are photographs of fluoresced rhodamine labeled cochleates containing fluorescein isothiocyanate (FITC) labeled morpholinos. FIGS. 1C and 1D depict cochleates containing morpholinos, morpholinos that have been released into the cytosol from unwrapped cochleates, and the delivery of FITC labeled anti-GAPDH Morpholino into the cytoplasm. The morpholinos delivered into the cells depicted in these FIGS. 1A-D were retained in the cells for at least 72 hours. The labeled morpholinos were delivered into the cell cytosol and nucleus (FIGS. 1C and 1D).

Figure 4A:
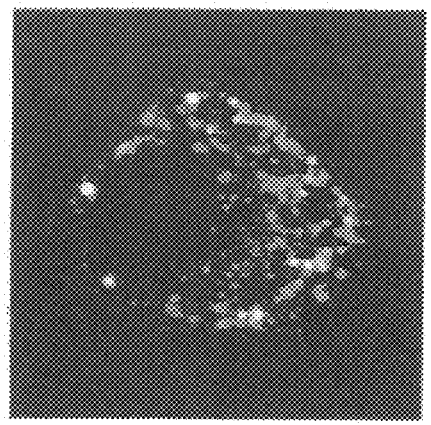
FIGS. 4A-B are photographs of cells treated with morpholino-cochleates demonstrating delivery of the morpholinos into the cell cytosol and nucleus.
Figure 4B:
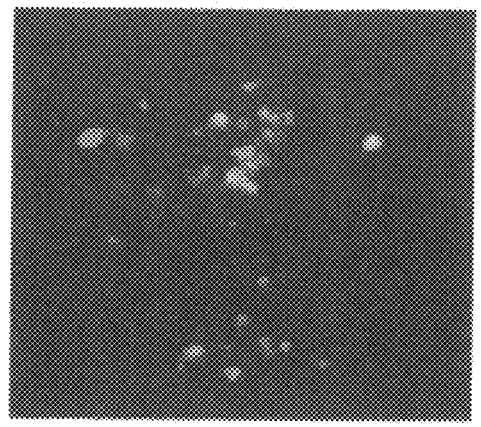

As shown in FIGS. 4A-B, the cochleates fuse or are taken up by the cells and form submembrane aggregates. FIG. 4A shows intracellular rhodamine cochleates (punctuate and diffuse red color) after 3 hours. Yellow, yellow-green and orange-red indicate cochleates containing morpholinos. FIG. 4B shows delivery 12 hours after cochleate introduction. Rhodamine labeled lipid, originally in cochleates, is largely distributed to the cellular membranes although there appears to be accumulation within the cell, suggesting that some empty cochleates may be sequestered in vacuoles, while FITC-labeled morpholinos (green color) have been released into the cytosol from unwrapped cochleates by 12 hr. after initial presentation to the cell.

Figure 3:
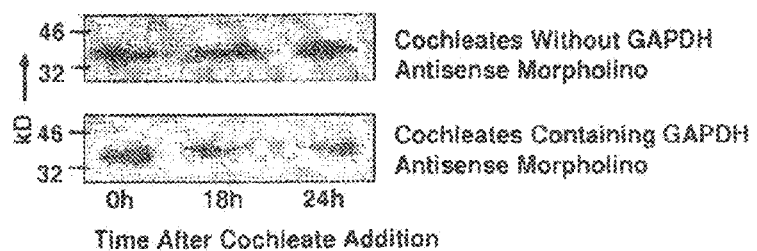
FIG. 3 includes two Western blots illustrating a decrease in glyceraldehyde-3-phosphate dehydrogenase (GAPDH) protein at 18 and 24 hours following treatment with a GAPDH antisense morpholino-cochleate (lower blot) while control cells receiving vehicle with cochleate alone (upper blot) showed no change in GAPDH protein levels.

As shown in FIG. 3, Western blotting for GAPDH protein in these labeled cells showed a time dependent decrease in GAPDH protein levels by 18-24 hours following treatment with cochleates with GAPDH antisense morpholino (lower blot) while control cells receiving vehicle with cochleate alone (upper blot) showed no change in GAPDH protein levels. This example demonstrates that morpholino-cochleates are an efficient technique for delivering antisense morpholinos in a manner that does not compromise the integrity of the cells. Plain cochleates or cochleates with sense morpholino at the same concentration had no toxicity.

Example 3

Delivery of Morpholinos Via Cochleates into Retinal Ganglion Cells

Figure 2A:
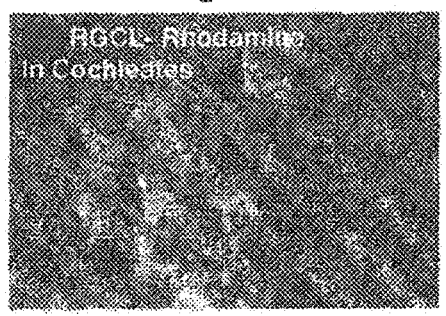
FIGS. 2A-B are photographs of X-Y RGCL LCSM computational slices demonstrating avid cochleate uptake by retinal ganglion cells in situ.
Figure 2B:
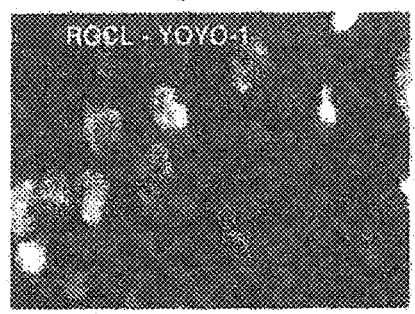

Morpholino-cochleates were prepared as described in Example 1 with FITC-labeled GAPDH morpholinos. These morpholino-cochleates were administered to retinal ganglion cells in situ in retinal organotype culture. It was observed that the morpholino-cochleates readily interacted with the cells in the retinal ganglion cell layer (FIGS. 2A and 2B). FIGS. 2A and 2B are images of X-Y RGCL LCSM computational slices demonstrating avid cochleate uptake by retinal ganglion cells in situ. Scale bars indicate 10 micrometers.

FIG. 2A indicates cochleate delivery and biological activity of the antisense molecules. Interference with GAPDH by the antisense molecule triggers apoptosis, detected here by YOYO staining of all the retinal ganglion cells in the field. Cell nuclei with apoptotic chromatin condensation have very bright homogeneous YOYO signals (See FIG. 2B). This system provides a very efficient technique for delivering antisense oligonucleotides in a manner that does not compromise the integrity of the cells. In sharp contrast, other delivery methods were associated with some cytotoxicity and a maximum of 10% transfection.

Example 4

Cochleate Delivery of Antisense DNA in a Murine Model of Chronic Lymphocytic Leukemia NZB mice develop a B-1 cell lymphoproliferative disorder that serves as a murine model of chronic lymphocytic leukemia (CLL). These malignant B-1 cells produce significantly higher levels of IL-10 mRNA than normal B-1 or B cells. The addition of antisense oligodeoxynucleotides specific for IL-10 mRNA dramatically inhibits the growth of leukemic B-1 cells in a time and dose dependent manner. Control cell lines that do not depend on IL-10 for growth are not affected. In vitro antisense therapy targeted at the 5' region of the IL-10 mRNA not only resulted in inhibition of malignant B-1 cell proliferation, but also inhibited IL-10 production by malignant B-1 cells. In vivo, antisense therapy was effective in preventing death of the animals due to uncontrolled growth of $5 \times 10^6$ intraperitoneally transferred malignant B-1 cells. In these experiments, after approximately 6 weeks, at which time the control animals had all died, the antisense IL-10 treated groups had no evidence of disease.

Comparison of Cochleates and Mini-Osmotic Pump

Cochleates were much more effective in delivering antisense IL-10 oligonucleotide for preventing the growth of malignant B-1 cells in vivo, and protecting against disease and death. Using a mini-osmotic infusion pump, 300 ug/day phosphorothioate-modified antisense IL-10 oligonucleotide was constantly infused for 28 days, totaling 8.4 mg. Lower quantities or shorter times did not result in protection from tumor cell challenge.

Although phosphorothioate oligos are known to have much longer half lives in vivo, much lower doses of unmodified phosphodiester antisense IL-10 oligonucleotides were effective when formulated and delivered in cochleates. Four injections (days 0, 5, 8, and 14) of antisense IL-10 cochleates, totaling 1.3 mg, prevented the growth of malignant B-1 cells. The reasons for this increased efficacy of unmodified antisense IL-10 when delivered in cochleates may be due to the prevention of nuclease degradation in plasma and interstitial fluid, delivery of the intact oligonucleotide directly into the cytoplasm of the target cell, and/or slow delivery over a prolonged period of time, due to the multilayered nature of the cochleates.

Cochleate Delivery of Antisense DNA Protects Against B Cell Lymphoma

Figure 5:
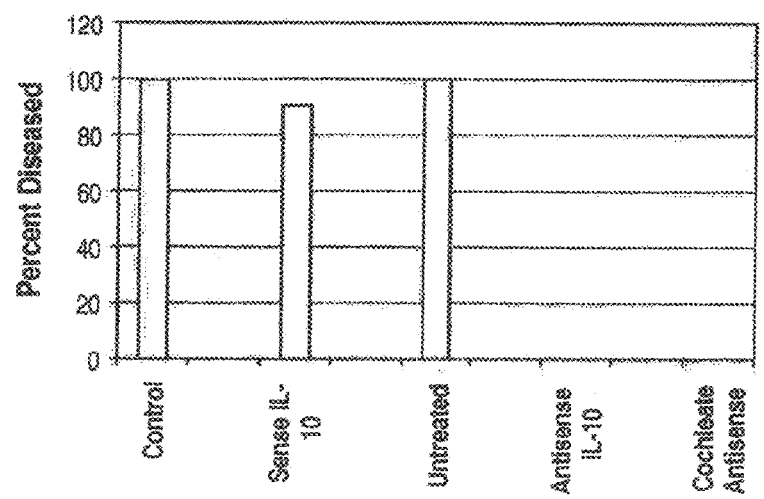
FIG. 5 is a graph summarizing in vivo antisense IL-10 experiments set forth Example 4.

FIG. 5 summarizes in vivo antisense IL-10 experiments including both forms of delivery, pumps and cochleates. All mice were (NZB DBA/2) F1 recipients that received a transfer of leukemic B-1 cells. The percent of diseased animals in a particular treatment group is the number of diseased animals divided by the animals studied, multiplied by 100. Disease includes all mice that died before day 60 with hind leg paralysis or evidence of clones of malignant B-1 cells detected by flow cytometry or abnormal pathology at the time of sacrifice. Mini infusion pump antisense IL-10 treated animals (0/4), Antisense IL-10-Cochleate treated animals (0/3), sense IL-10 (4/5), control (receiving either pumps and buffer alone or cochleates alone) (7/7), untreated receiving no treatment following transfer of the malignant B-1 cells (7/7).

This example demonstrates successful cochleate delivery of an antisense molecule in vivo, wherein biological activity was retained.

Example 5

Delivery of Morpholino-Cochleates to Rats with Induced Parkinson's Disease-Like Pathology Parkinson's disease-like pathology with be induced in rats with CSF-delivered rotenone and joint rotenone-CLβL cerebrospinal fluid (CSF) delivery. Morpholino-cochleates will be used to deliver morpholinos to suppress GAPDH and p53 protein levels to study its effect on NSdn apoptosis and protein aggregation caused by the CSF infusion.

Based on studies in cultured cells and the findings of Greenamyre et al., it is expected that chronic CSF-delivered rotenone will induce PD-like pathology in the rats at lower dosages than those found for rats with intravenous delivery and that joint rotenone-CLβL CSF delivery will markedly shift the concentration dependence to lower values. Based on previous studies in culture, it is expected that both the p53 and GAPDH antisense will reduce NSdn apoptosis and may also decrease any protein aggregation caused by the CSF infusion. The GAPDH antisense treatment should not affect p53 levels or subcellular localization while the p53 antisense treatment should prevent both GAPDH upregulation and nuclear accumulation.

Morpholino-cochleates will be employed to induce non-lethal reductions in GAPDH (see FIG. 3 in which GAPDH was reduced to about 50%), and p53 proteins. High GAPDH morpholino-cochleate concentrations resulting in marked GAPDH reductions cause cellular death over 3 to 8 hours, probably due to a failure of glycolysis. The morpholino oligos from Example 1 from GeneTools, LLC (Philomath, Oreg.) will be used. For p53 antisense and mismatch, 5'TCATATC-CGACTGTGAATCCTCCAT3' (SEQ ID NO.: 3) and 5'TCATTTCCGTCTGTGTATCCTGCAT3' (SEQ ID NO.: 4), respectively, will be used. These sequences have been used to block GAPDH and p53 synthesis (Chen et al. (1999) J Neurosci. 19:9654-62; Fukuhara et al. (2001) Neuroreport 12:2049-52), and target the first 25 bases of each coding sequence. Three other series of sequences will be used that have previously altered either p53 or GAPDH synthesis.

Since both the cochleates and the morpholinos can be fluorescently labeled as described above and are retained in cells after paraformaldehyde fixation, it should be possible to observe the proportion of cells that concentrate the carrier and the morpholino before collecting lysates from ventral mesencephalon to measure the overall reduction in GAPDH or p53 protein. Furthermore, fluorescence labeling should allow a determination of whether specific SNc cellular phenotypes showing evidence of apoptosis or protein aggregation also took up the cochleates.

Similar to preliminary studies with retrograde tracers (Yee et al., (1994) Cell Mol Neurobiol 14:475-86; Shimizu et al. (2001) J Cereb Blood Flow Metab 21:233-43), the antisense and mismatch oligonucleotides will be infused into the lateral ventricle using a cannulae system. Morpholinos will be carried into NSdns and other cells from the CSF by the cochleates. Zarif et al. (2000) Adv Exp Med Biol 465:83-93. Rhodamine can be included in the lipid constituents of the cochleates and will allow the visualization of the binding of the cochleate to the outer membranes of the cell using LCSM fluorescence imaging as illustrated in FIGS. 1A-D.

Both the oligomeric specific and oligomeric non-specific antibodies will be employed to determine whether all or part of the immunoreaction in a specific subcellular locus is due to a specific oligomer of GAPDH. Monoclonal antibody that specifically recognizes GAPDH monomer or dimer but not GAPDH tetramer will be obtained from Ono Pharmaceuticals (Japan). Also used will be a sheep polyclonal antibody that only recognizes GAPDH tetramer and a mouse monoclonal antibody that recognizes all oligomeric forms of GAPDH. Carlile et al. (2000) Mol. Pharmacol. 57:2-12. Co-staining with YOYO-1 will be used to differentiate the nuclear and non-nuclear compartments. Carlile et al. (2000) Mol. Pharmacol. 57:2-12.

In order to quantitate immunofluorescence for different antibodies and different treatments, sections will be incubated for different treatments together to ensure identical exposure to antibodies. Fluorescence intensity will be measured from within 3 extra nuclear 4 µm×4 µm regions within the somata of randomly chosen neurons using the program Northern Eclipse (Empix Imaging, Mississauga, Ontario). Three measurements will be made immediately outside each neuronal somata in order to determine intraneuronal fluorescence above background. Tsuda et al. (1994) Neuron 13:727-36. Approximately 600 neurons will be examined for each animal and 7200 for each concentration time. The program allows the coordinates of each measurement to be retained so that measurements can be made for identical loci from simultaneously collected images for different antibodies.

It is expected that both p53 tumor suppressor protein and GAPDH will undergo increases and nuclear accumulation in response to rotenone or CLβL exposure. Rotenone will only increase the proteins in NSdns while CLβL will increase them in all SNc cells. It is expected that a proportion of the neurons will show dense nuclear immunofluorescence for the antibody against GAPDH monomer/dimer and for the antibody against all GAPDH oligomeric forms, but not for the antibody that only recognizes tetramer. A follow-up study has been conducted on our studies in Parkinson's Disease (PD) postmortem SNc (Tatton, Exp Neurol 166:29-43 (2000)), using the antibody that recognizes all GAPDH oligomers with similar examinations using the monomer/dimer selective antibody. It was found that GAPDH nuclear accumulation in PD postmortem SNc involves only the monomer/dimer. It will be valuable to determine if the model shows the same oligomeric selectivity.

Example 6 siRNA-Cochleates for the Treatment of Fungal Infections

These studies will determine the relative effectiveness of siRNA-cochleates compositions for preventing invasive Aspergillosis in animal models that mimic disease in humans. Female BalbC or DBA2 mice from Charles River Labs will be used for this study because they behave in a reliable manner when infected with fungal pathogens. Previous studies have shown that intravenous inoculation with pathogenic fungi in mice produces an infection similar to that seen in man.

*Aspergillus fumigatus* $H^+$-ATPase will be studied as an effect therapeutic target for antifungal agents employing siRNA-cochleates of the invention. The plasma membrane $H^+$-ATPase from *Candida albicans* was cloned and characterized. Monk, B. C., et al. (1991) J Bacteriol. 173(21): 6826-36. Similar cloning and characterization projects have been completed on plasma membrane $H^+$-ATPases from *Cryptococcus neoformans* (Soteropoulos, P., et al. (2000) Antimicrob Agents Chemother 44(9): 2349-55) and *Aspergillus fumigatus* (Burghoorn, H. P et al. (2002) Antimicrob Agents Chemother 46(3):615-24).

The gene, AfPMA1, encoding the plasma membrane proton pump ($H^+$-ATPase) of *Aspergillus fumigatus* was characterized from *Aspergillus fumigatus* strain NIH 5233 and clinical isolate H11-20. An open reading frame of 3109 nucleotides with two introns near the N-terminus predicts a protein consisting of 989 amino acids with a molecular weight of approximately 108 kDa. The predicted *Aspergillus fumigatus* enzyme is 89% and 51% identical to $H^+$-ATPases of *A. nidulans* and *S. cerevisiae*, respectively. AfPMA1 is a typical member of the class III P-type ATPase family that contains 10 predicted transmembrane segments and conserved sequence motifs, TGESL (SEQ ID NO.: 13), CSDKTG (SEQ ID NO.: 14), MXTGD (SEQ ID NO.: 15) and GDGXNDXP (SEQ ID NO.: 16) within the catalytic region. The enzyme represents 2% of the total plasma membrane protein, and it is characteristically inhibited by orthovanadate with an $IC_{50}$~0.8 µM. The $H^+$-ATPase from *Aspergillus* spp. contains a highly acidic insertion region of 60 amino acids between transmembrane segments 2 and 3 which was confirmed in the membrane assembled-enzyme with a peptide-derived antibody. Increasing gene copy number of AfPMA1 confers enhanced growth in low pH medium consistent with its role as a proton pump. Burghoorn, H. P. et al. (2002) 46(3):615-24.

Cell Phenotype and Morphology Changes Will be Evaluated for *Aspergillus fumigatus*

The normal septate hyphae are wide and form dichotomous branching, i.e., a single hypha branches into two even hyphae, and then the mycelium continues branching in this fashion. It was observed that sublethal amount of anti-H+-ATPase antagonists like ebselen produce long thin hyphal elements with diminished branching. As the $H^+$-ATPase activity is diminished, increasing cell surface area helps maintain the overall capacity of the system by increasing the number of pumps. It is expected, that stressing the mutant proton pumps by acidifying the cytoplasm with weak acids at low external medium pH will show similar results. *Aspergillus* is particularly resistant to high temperature and grows efficiently at 45° C. It was observed that the MIC for cell killing with ebselen is decreased with increasing temperature. Whether inhibition of PMA1 alters the temperature profile for growth will be determined. Finally, spore formation and spore germination will be examined in a similar manner.

The essential role of the H+-ATPase in spore germination and multiplication of growing cells provides an opportunity to explore the ability of nanocochleates to efficiently deliver siRNAs targeted to the H+-ATPase of *A. fumigatus*. Given the medical importance of *A. fumigatus* and the paucity of available antifungal compounds, siRNA cochleate compositions have the potential to be effective therapeutic alternatives.

The goal is to determine the feasibility and technical merit of preparing and testing stabilized siRNA-cochleate compositions that will enhance the antifungal activity of these oligonucleotides.

Stable compositions of nanocochleates containing siRNA targeting *Aspergillus fumigatus* $H^+$-ATPase are to be prepared, and that these compositions will be capable of interacting with and inhibiting the growth of *Aspergillus fumigatus* both in vitro and in vivo.

Standard protocols will be used to prepare siRNA-cochleates. Lipid (PS) to siRNA ratios will range from 25:1 to 100:1, wt:wt. Purified siRNA molecules will be purchased from commercial vendors.

To stabilize the particle size of the cochleate compositions, several commercially available, FDA approved excipients will be evaluated for their ability to stabilize size characteristics of the cochleate compositions. Excipient candidates will be chosen that have the potential to interact with the cochleate surface and prevent cochleate-cochleate interaction. E.g., excipients that contain hydrophilic polymers (e.g., polyethyleneglycol (PEG)) with/or without a hydrophobic tail can be used. Excipients with properties that mimic casein, which is a highly phosphorylated, calcium-binding molecule also will be tested.

*Aspergillus fumigatus* PMA1 siRNA

To investigate gene silencing by RNA interference as a potential therapeutic in pathogenic fungi, small interference RNA (siRNA) were designed to the PMA1 gene of *Aspergillus fumigatus*. PMA1 encodes the essential plasma membrane proton-ATPase, which regulates electrochemical proton gradients and intracellular pH in this pathogenic organism. Miller, M. D. et al. (1992) J Exp Med 176:1739-1744. Two PMA1 sense and antisense siRNA pairs (21mers) were designed to regions 100 and 162 nucleotides downstream of the start codon (Genbank/NCBI accession number AY040609) using Qiagen's siRNA design tool (python.penguindreams.net/Xeragon_Order Entry/jsp/SearchByAccessionNumber.jsp). The siRNA sequences are listed in Table I. Burghoorn, H. P. et al. (2002) Antimicrob Agents Chemother 46:615-24.

Imaging, General Methods.

An Olympus FV500 confocal laser scanning microscope will be used to obtain images of fluoresce-tagged cochleates in real time from living cells and from fixed tissue in order to investigate the dynamics of cochleate uptake by macrophages and fungus. A Hitachi S4700 field emission scanning electron microscope (FESEM) will be used to investigate details of cochleate ultrastructure and provide ultra-high resolution images of cochleate-cell membrane/wall interactions.

Confocal Imaging

A) Cochleate uptake over time. Cells/fungi will be exposed to cochleates for 2, 5, 10, 15, 30, 60 min., 12 h, 24 h, 48 h to establish a temporal sequence for uptake and dispersal. Cells/fungi will be fixed with 2% gluteraldehyde (EM grade) and will be exposed to other cell markers for colocalization. For real-time imaging, coverslips are transferred to a environmentally controlled sealed chamber.

B) Subcellular localization. Cell nuclei marked with Alexa 488-histone 1 will be used in live cells to determine whether siRNA localizes in the nucleus. Lysotracker probes, which mark lysosomes, will help determine if cochleates and/or their contents are found in lysosomes. Tarasova N. I. et al. (1997) J. Biol. Chem. 272: 14817-14824. A cationic linear polyene, TMA-DPH, a lipid marker for endocyotsis and exocytosis, (Kawasaki Y. et al. (1991) BBBA 1067: 71-80; Illinger D. et al. (1993) Biol. Cell 79: 265-268) will assist in determining how cochleates are absorbed/released by macrophages. All markers are available at Molecular Probes (Oregon)

FESEM Imaging

Rapid freezing of unfixed, bulk biological samples such as cochleates and cells/fungi will produce the least distortion in the specimens. However, it will be necessary to test alternate protocols to see what additional information about cochleate/cell interactions may be obtained.

A) Double Coating of Unfixed, Frozen, Hydrated Samples. A nitrogen slush will be used to cool down unfixed, hydrated biological samples and then perform a double coating layer (2 nm platinum, followed by 5-10 nM carbon) to allow high resolution backscattered electron detection (Walther P. et al. (1997) Scanning 19:343-348).

B) Cryopreserved Samples. 30% sucrose and 20% sucrose/3% PEG-400 cryopreservation methods will be tested on fixed samples. This method will likely not provide ultra high resolution images as in double-coating, but may be best for preparing composite and topographic EM images at lower accelerating voltages.

TABLE I

*A. fumigatus* PMA1 siRNA sequences

| cDNA Target Sequence | Region | Sense siRNA (5'-3') | Antisense siRNA (3'-5') |
|---|---|---|---|
| AACCGTTACATC TCGACTGCT (SEQ ID NO.: 5) | 100 nt downstream from start codon | CCGUUACAUCUC GACUGCUdTdT (SEQ ID NO.: 6) | dTdTGGCAAUGUA GAGCUGACGA (SEQ ID NO.: 7) |
| AAGCCTCCAGCA GAAGAAGAA (SEQ ID NO.: 8) | 162 nt downstream from start codon | GCCUCCAGCAGA AGAAGAAdTdT (SEQ ID NO.: 9) | dTdTCGGAGGUCG UCUUCUUCUU (SEQ ID NO.: 10) |

The characterization of siRNA cochleate compositions will be performed using standard protocols including biochemical analysis (lipid and drug quantitation and integrity), morphology (light and electron microscopy), and particle sizing.

C) Fixed Dehydrated, Critical Point Dried Samples. Method A may be too damaging to fungi, in which case a critical point drying method (Muller, W. H. et al. (2000) 22:295-303) will be used that can also be used for mammalian cells to provide high resolution imaging. This method will provide high resolution images. However, this method can produce more distortion of the sample than A or B.

Example 7

Methods of Making siRNA-Cochleates Directed Against the Expression of erbB Protein Labelled siRNA (Sense: 5'-UCCCGAGGGCCGGUAUA-CATT-3' (SEQ ID NO.: 11); Antisense: 5'-UGUAUACCG-GCCCUCGGGATT-3' (SEQ ID NO.: 12) directed against erbB (targeting codons 852-873 of the mRNA encoding erb) were obtained from PPD, Inc. (Wilmington, N.C.). siRNA were Cy5 labelled or FITC labeled for various experiments as indicated in the below experiments. The annealed 22 bp siRNA 20 micromolar stock solution included 0.26 µg siRNA/µl. The siRNA buffer contained either (i) 100 mM potassium acetate, 30 mM HEPES-KOH (pH7.4), and 2 mM magnesium acetate; or (ii) 20 mM KCl, 6 mM HEPES (pH 7.5), and 0.2 mM magnesium chloride.

Stock liposome suspensions were prepared by solubilizing DOPS powder alone, or DOPS powder (99% by weight) and Rhodamine PE (1% by weight), in chloroform, drying to film under nitrogen, and rehydration in TES buffer (pH 7.4) to a concentration of 10 mg/ml by vortexing.

Cochleates were prepared from liposomes as described above using the following methods. In the following methods, unless otherwise indicated, the DOPS:siRNA weight ratio was 50:1, and methods were carried out at neutral pH conditions with approximately isotonic salt concentrations.

Trapping Method. 6.5 µl of stock liposome suspension was filtered with a 0.2 micron filtration membrane to obtain small unilamellar vesicle liposomes (SUVs). 5 µl of the stock siRNA solution (1.3 µg siRNA) was placed in an Eppendorf micro-centrifuge tube, and the 6.5 µl SUV suspension (65 µg DOPS lipid) was added to the siRNA. 88.5 µl TES Buffer was added and mixed well, followed by addition of 8 µl of 0.1M calcium chloride and mixed well to form cochleates.

Extrusion Method. 5 µl of the 20 µmM stock siRNA solution (1.3 µg siRNA) was placed in an Eppendorf micro-centrifuge tube. 6.5 µl DOPS liposome suspension (65 µg lipid) from the 10 mg/ml suspension was added to the siRNA. 88.5 µl of TES buffer was added and the mixture extruded 7 times with an Avanti mini-extruder, which allows production of unilamellar lipid vesicles by multiple extrusions between two connected syringes through a polycarbonate membrane with defined pore size. Membrane used was 0.2 microns pore size. 7 µl of 0.04M calcium chloride was added and mixed well to form cochleates.

Alternative Extrusion Method 25 µl of the 20 µmM stock siRNA solution (6.5 µg siRNA) was placed in an Eppendorf micro-centrifuge tube. 25 µl unfiltered DOPS liposome suspension (250 µg lipid) from the 10 mg/ml suspension was added to the siRNA. The mixture was extruded 7 times. 6 µl of 0.05M calcium chloride solution was added and mixed well to form cochleates. The lipid:siRNA ratio was 39:1 wt/wt.

Cochleate Conversion Method. 65 µl DOPS liposome suspension from the 10 mg/ml suspension was placed in an Eppendorf micro-centrifuge tube. 4 µl of 0.1M calcium chloride solution was added and mixed well to form cochleates in suspension. 7 µl of this suspension was added to another micro-centrifuge tube, and centrifuged at 13,00 RPM for 30 minutes. The supernatant was removed, and 5 µl of the 20 µmM stock siRNA solution (1.3 µg siRNA) was added to the cochleates. 3 µl of 150 mM EDTA was added to convert the cochleates to liposomes associated with the siRNA. 8 µl of 0.01M calcium chloride solution was added and mixed well, followed by the addition of 80 µl of TES buffer and 2 mM calcium chloride and mixing.

Example 8 siRNA-Cochleates Directed Against the Expression of erbB Protein

Employing the siRNA identified and liposome stock solutions prepared in Example 7, siRNA cochleates were prepared and administered to ovarian cancer cell line SKOV3 (PPD, Inc.). In the following methods, the DOPS:siRNA weight ratio was 2:1 (12.45 µg lipid, 6.5 µg siRNA). The lipid concentration in the liposomes was about 100 µg/ml (0.1 mg/ml), the siRNA concentration approximately 57 µg/ml (0.057 mg/ml). SKOV3 cells were grown in monolayers in humidified air with 5% $CO_2$ at 37° C. in 60 $mm^2$ Petri dishes (Corning) containing 5 mL of DMEM supplemented with 10% FBS. The calcium concentration in mix was 130 mM for the elevated or high calcium method, and 3.8 mM for the low or depressed calcium method.

High Calcium Method. 25 µl of the 20 µM stock siRNA solution was placed in an Eppendorf micro-centrifuge tube to which 6 µl of 2.5M calcium chloride solution was added and mixed well. 83 µl of DOPS liposomes at 150 µg/ml in TES (pH 7.0) was added, followed by 17 µl of TES Buffer. The total volume (131 µl) was mixed well. 5 µl of the mixture was then added to 45 µl cell culture medium and incubated for 72 hours at 37° C. The culture was fixed and stained with antibodies for erbB2 expression.

Low Calcium Method. 25 µl of the 20 µmM stock siRNA solution was placed in an Eppendorf micro-centrifuge tube to which 5 µl of 0.1M calcium chloride solution was added and mixed well. 83 µl of DOPS liposomes at 150 µg/ml in TES (pH 7.0) was added, followed by 17 µl of TES Buffer. The total volume (131 µl) was mixed well. 5 µl of the mixture was then added to 45 µl cell culture medium and incubated for 72 hours at 37° C. The culture was fixed and stained with antibodies for erbB2 expression.

Control Preparations. SKOV3 cells were also incubated with empty cochleates made employing the same methods (except without addition of siRNA) and Lipofectamine formulated siRNA. The cultures were also fixed and stained with antibodies for erbB2 expression.

Partial Knockdown of erbB2 in SKOV3 Cells

Figure 6:
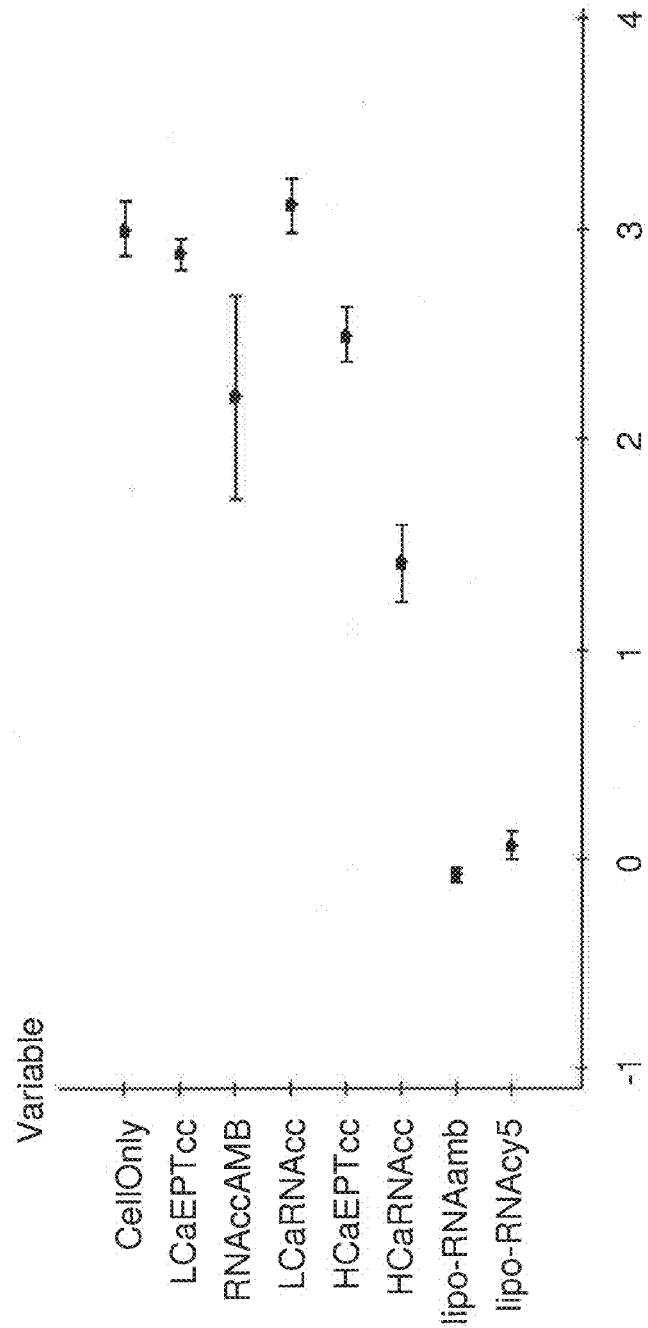
FIG. 6 is a graph of absorption due to color development in the ELISA assay for surface erb B2 expression in SKOV cells for siRNA-cochleates, empty cochleates, and Lipofectamine formulated siRNA against erb B2 expression.

Absorption results (ELISA assay) for surface erb B2 expression for each of the treated cultures are shown in FIG. 6. Decreased absorption indicates inhibition of Erb B2 by specific or non-specific mechanisms. The low calcium siRNA cochleate composition (LCaRNAcc) did not appear to inhibit Erb B2 compared to empty cochleates (LCaEPTcc). Whereas, the high calcium siRNA-cochleate composition did (HCaRNAcc vs. HCaEPTcc). Less staining of wells treated with Lipofectamine formulated siRNA (lipo-RNAamb and lipo-RNA-Cy5) may be due to specific inhibition combined with non-specific down regulation and fewer cells associated with greater cellular cytotoxicity.

Figure 7:
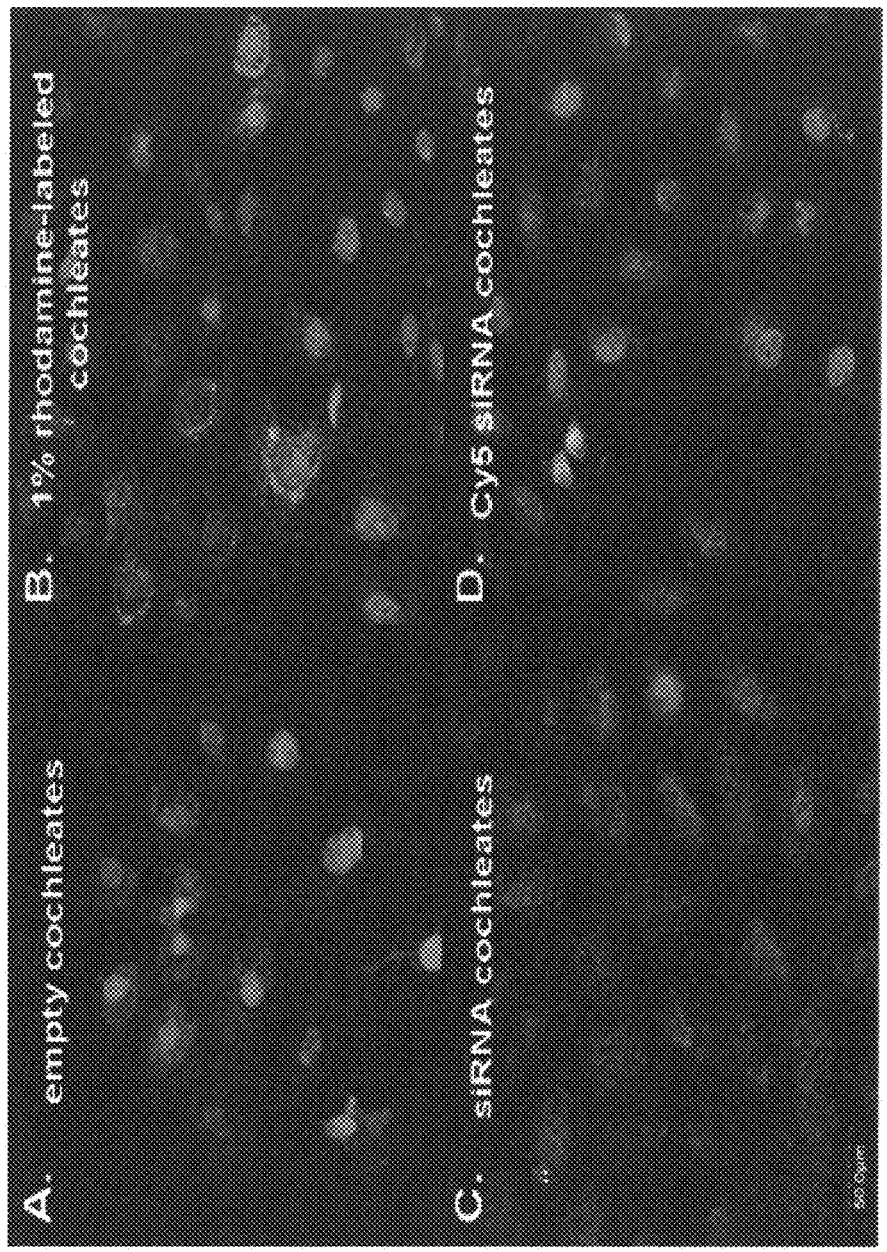
FIG. 7 is a series of fluorescent confocal microscopy images of the SKOV3 cells 24 hours post-exposure to: empty cochleates (panel A), 1% rhodamine-labelled cochleates (panel B), anti-erb B2 siRNA-cochleates (panel C), and Cy5 labelled anti-erb B2 siRNA-cochleates (panel D), indicating successful delivery of siRNA to the cells and partial knockdown of cytoplasmic erb B2 expression.

FIG. 7 is a series of fluorescent confocal microscopy images of the SKOV3 cells 24 hours post-exposure to: empty cochleates (panel A), 1% rhodamine-labelled cochleates (panel B), anti-erb B2 siRNA-cochleates (panel C), and Cy5 labelled anti-erb B2 siRNA-cochleates (panel D). The cochleates images in panel C and panel D were manufactured using the high calcium method described above. Partial knockdown of cytoplasmic erb B2 by anti erb B2 siRNA-cochleates was observed (panel C and panel D), as well as confirmation of intracellular delivery and localization of cochleates and siRNA around the nucleus (panel B and panel D). Additionally, the subcellular distribution of Rhodamine-labelled cochleates (panel B) and Cy5 siRNA-cochleates (panel D) appears to be different, indicating delivery and release of siRNA.

Figure 8:
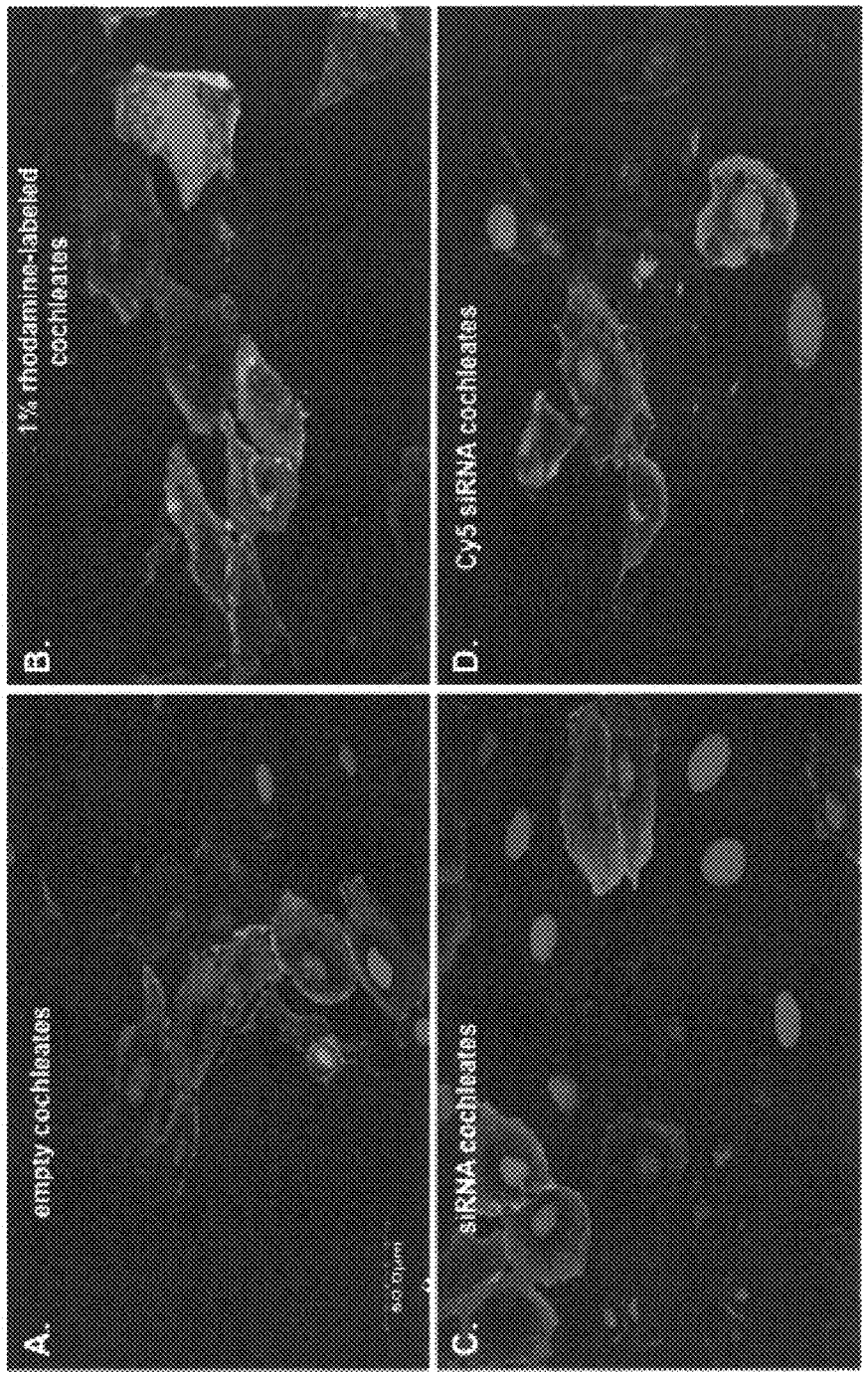
FIG. 8 is a series of confocal microscopy images of SKOV3 cells 24 hours post-exposure to: empty cochleates (panel A), 1% rhodamine-labelled cochleates (panel B), anti-erb B2 siRNA-cochleates (panel C), and Cy5 labelled anti-erb B2 siRNA-cochleates (panel D), indicating successful delivery of siRNA to the cells and partial knockdown of cell surface erb B2 expression.

FIG. 8 is a series of confocal microscopy images of SKOV3 cells 24 hours post-exposure to: empty cochleates (panel A), 1% rhodamine-labelled cochleates (panel B), anti-erb B2 siRNA-cochleates (panel C), and Cy5 labelled anti-erb B2 siRNA-cochleates (panel D). Partial knockdown of membrane-localized erbB2 in SKOV3 cells after exposure to siRNA(erbB2) cochleates was observed (panel C and panel D). Also, intracellular delivery of rhodamine cochleates (panel B) and Cy5 labeled siRNA (panel D) is observed.

Example 9

Cochleates Prepared with siRNA-PEI Complexes siRNA and polyethylenimine (PEI) were allowed to associate to form a positively charged complex and then bound to negatively charged liposomes and encochleated. The effect of these encochleated complexes was studied.

22.5 µl of siRNA(20 µM) was added to an Eppendorf micro-centrifuge tube. 16.2 µl of PEI (2000 MW, Lupasol G35, BASF) at a concentration of 0.05%, was added and mixed well. Then, 116 µl of pre-made DOPS liposome at 1.5 mg/ml (in TES, pH7.0) was added to this mixture and mixed well. Finally, 115 µl of 0.1M calcium chloride was added and mixed well to form cochleates. Cochleate morphology was confirmed microscopically. In order remove any free (unencochleated) siRNA from the siRNA-cochleate composition, the siRNA-cochleates were pelleted by centrifugation and the supernatants removed. Pellets were re-suspended.

Cochleates also were formed with non-specific siRNA (no specificity against erbB2 and no known intracellular target) according to the same method. The anti Erb siRNA-cochleates and non-specific siRNA-cochleates (both formed with PEI) were administered to SKOV3 cells at 0.25 µg (full dose) and 0.125 µg (50% dose), alongside untreated SKOV3 cells and were incubated for 72 hours.

Figure 9:
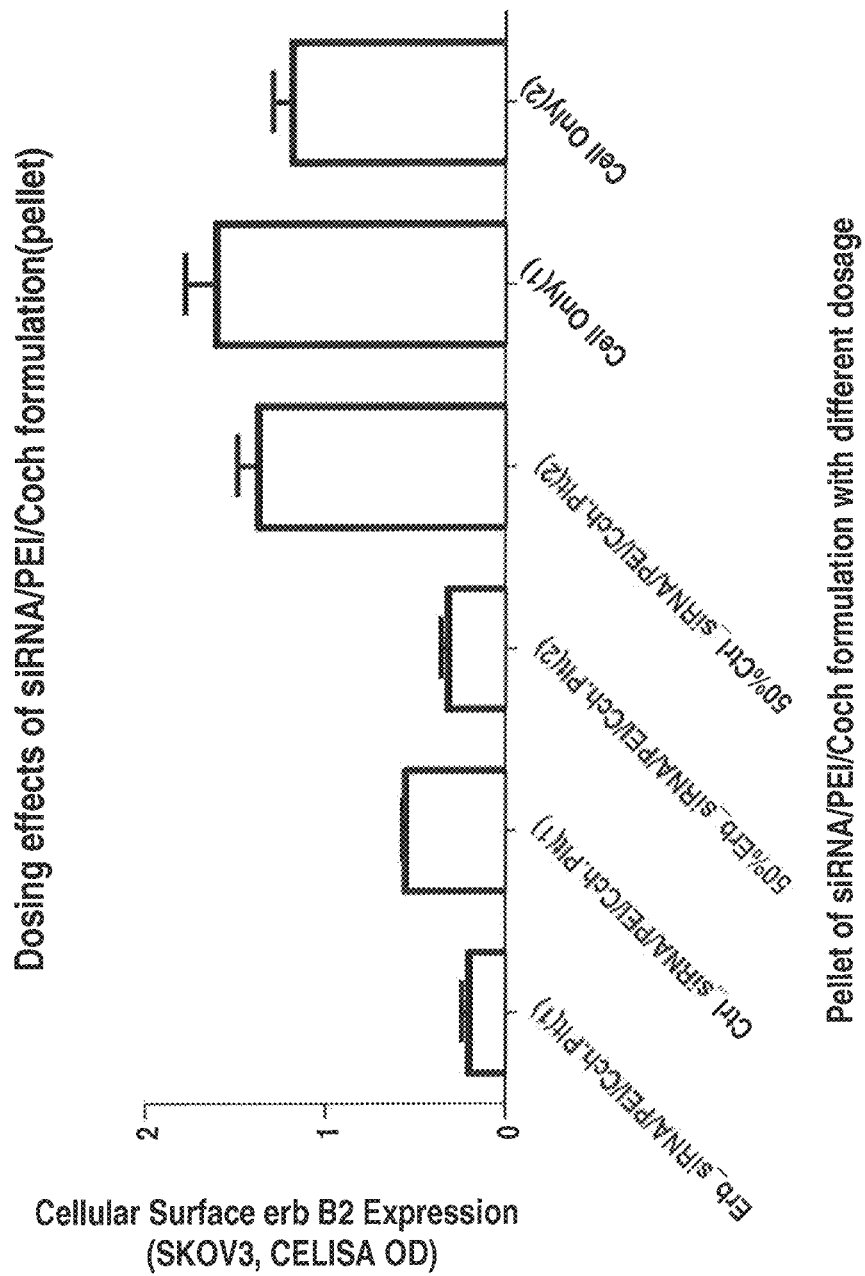
FIG. 9 is a graph indicating the partial knockdown effect of anti-erb B2 siRNA-cochleates formulated with PEI, and washed to remove free siRNA, on SKOV3 cells.

As summarized in FIG. 9, SKOV3 cells treated with the siRNA/PEI-cochleate compositions (Erb_siRNA/PEI/Cch.Plt (1)), showed a significant reduction in Erb B staining compared to untreated cells (Cell only (1)). Analogous compositions with a non-specific siRNA showed statistically less inhibition (CtrlErb_siRNA/PEI/Cch.Plt (1)). When half the concentration of siRNA/PEI-cochleates were used, the anti-Erb B siRNA/PEI-cochleates (ErbB Plt(2)) continued to cause a significant reduction in Erb B staining, but the control cochleates (Ctl.Plt(2)) showed no inhibition compared to untreated cells (Cell Only (2)). This indicates an anti-ErbB2-specific effect of the cochleate delivered siRNA.

The siRNA/PEI-cochleates were compared to SKOV3 cells treated with (1) unencochleated siRNA/PEI complex, (2) encochleated Fetal Bovine Serum (FBS) and PEI, (3) unencochleated FBS and PEI, and untreated cells. These controls were formulated by the same methods and in the same quantities and concentrations as the siRNA cochleates.

Figure 10:
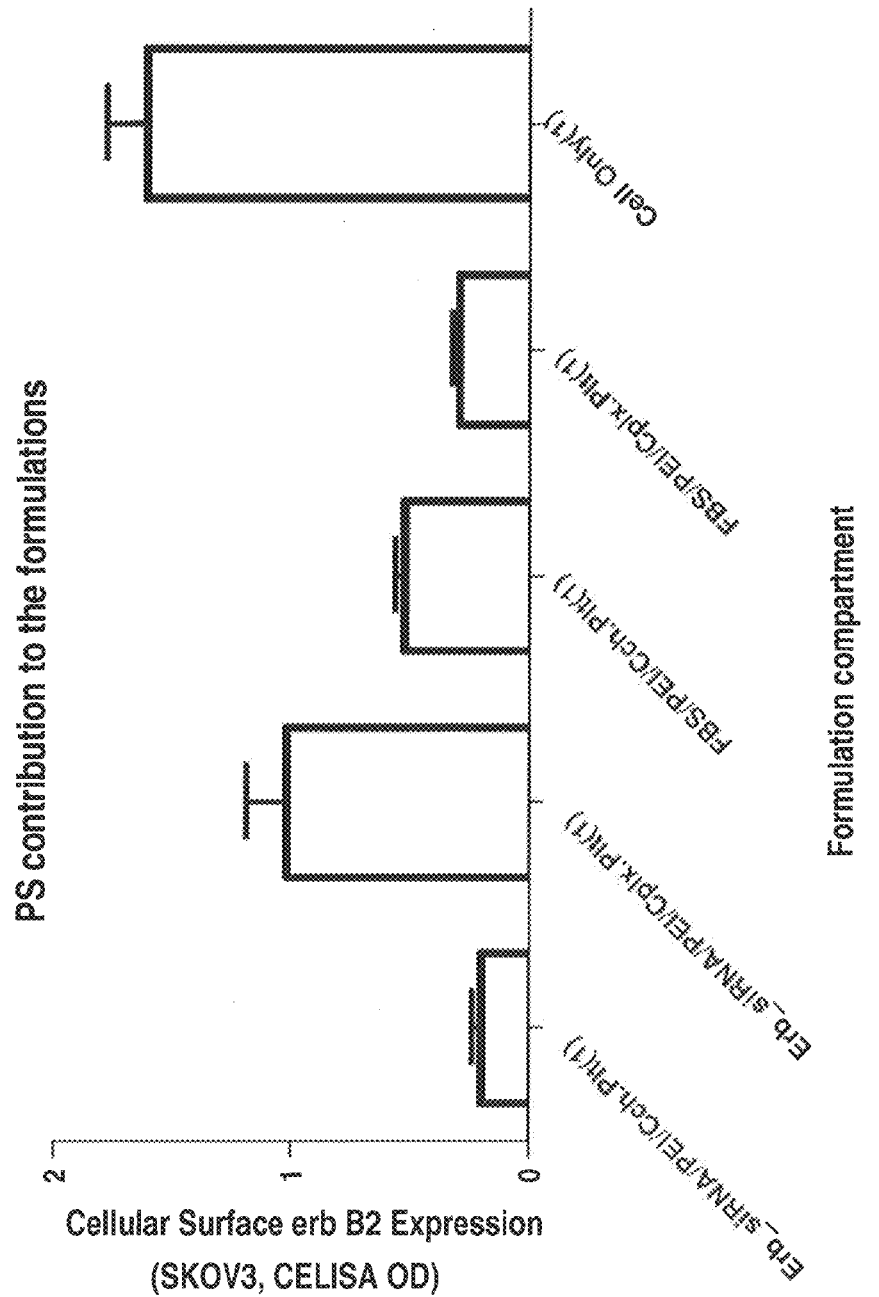
FIG. 10 is a graph indicating indicated increased RNAi effect in encochleated siRNA versus unencochleated siRNA in SKOV3 cells.

As summarized in FIG. 10, greater inhibition of Erb B was seen upon administration of siRNA/PEI-cochleates (Erb_siRNA/PEI/Cch.Plt(1)), as compared to the unencochleated siRNA/PEI (Erb_siRNA/PEI/Cplz.Plt(1)), indicating a positive role for cochleate delivery of siRNA. FBS/PEI-cochleates (FBS/PEI/Cch.Plt(1)), and unencochleated FBS/PEI (FBS/PEI/CplxPlt(1)), showed a decrease in staining due to cytotoxicity of un-complexed PEI.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An siRNA-cochleate composition comprising:
   a cochleate; and
   an siRNA associated with the cochleate,
   wherein the cochleate comprises a negatively charged lipid component and a multivalent cation component, wherein the siRNA is complexed with a transfection agent prior to contacting a liposome, wherein the transfection agent is a cationic transfection agent.

2. The siRNA-cochleate composition of claim 1, wherein the siRNA comprises at least one mismatch.

3. The siRNA-cochleate composition of claim 1, wherein the siRNA comprises at least one substitution.

4. The siRNA-cochleate composition of claim 1, wherein the siRNA is about 21-23 nucleotides long.

5. The siRNA-cochleate composition of claim 1, wherein the siRNA mediates RNA interference against a target mRNA.

6. The siRNA-cochleate composition of claim 5, wherein the target mRNA expresses a protein selected from the group consisting of: a cancer protein, a virus protein, an HIV protein, a fungus protein, a bacterial protein, an abnormal cellular protein and a normal protein.

7. The siRNA-cochleate composition of claim 1, further comprising a second siRNA directed against a second target mRNA.

8. The siRNA-cochleate composition of claim 1, further comprising at least one additional cargo moiety.

9. The siRNA-cochleate composition of claim 1, further comprising an aggregation inhibitor.

10. The siRNA-cochleate composition of claim 1, wherein the cationic transfection agent is selected from the group consisting of polyvinylamine, spermine, spermidine, histamine and a cationic lipid.

11. A method of forming an siRNA-cochleate composition comprising:
    complexing an siRNA with a transfection agent;
    contacting the complexed siRNA with a liposome; and
    precipitating the liposome and the complexed siRNA to form an siRNA-cochleate composition,
    wherein the cochleate comprises a negatively charged lipid component and a multivalent cation component, wherein the transfection agent is a cationic transfection agent.

12. The method of claim 11, comprising adjusting the pH of a liposomal suspension of the siRNA.

13. The method of claim 11, comprising charging the base pairs of the siRNA.

14. The method of claim 11, comprising using an elevated amount of calcium for precipitating the liposome and the siRNA.

15. The method of claim 11, comprising the step of extruding the liposome and the siRNA prior to precipitation.

16. The method of claim 11, wherein the cationic transfection agent is selected from the group consisting of polyvinylamine, spermine, spermidine, histamine and a cationic lipid.

* * * * *

SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atccgttgac accgaccttc accat                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atcccttgag accgagcttc tccat                                              25

<210> SEQ ID NO 3
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 3
tcatatccga ctgtgaatcc tccat                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcatttccgt ctgtgtatcc tgcat                                              25

<210> SEQ ID NO 5
<211> LENGTH: 21
<212> TYPE: DNA
<213> ORGANISM: Aspergillus fumigatus

<400> SEQUENCE: 5
aaccgttaca tctcgactgc t                                                  21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
ccguuacauc ucgacugcut t                                                  21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
agcagucgag auguaacggt t                                                  21

<210> SEQ ID NO 8
<211> LENGTH: 21
<212> TYPE: DNA
<213> ORGANISM: Aspergillus fumigatus

<400> SEQUENCE: 8
aagcctccag cagaagaaga a                                                  21

<210> SEQ ID NO 9
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
gccuccagca gaagaagaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
uucuucuucu gcuggaggct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ucccgagggc cgguauacat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
uguauaccgg cccucgggat t                                              21

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Gly Glu Ser Leu
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Cys Ser Asp Lys Thr Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid

<400> SEQUENCE: 15

Met Xaa Thr Gly Asp
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Any amino acid
<220> FEATURE:
<221> NAME/KEY: MOD_RES
<222> LOCATION: (7)
<223> OTHER INFORMATION: Any amino acid

<400> SEQUENCE: 16

Gly Asp Gly Xaa Asn Asp Xaa Pro
1               5
```